(12) United States Patent
Bucciaglia et al.

(10) Patent No.: US 8,523,898 B2
(45) Date of Patent: *Sep. 3, 2013

(54) ENDOSCOPIC ELECTROSURGICAL JAWS WITH OFFSET KNIFE

(75) Inventors: Joseph D. Bucciaglia, Louisville, CO (US); Edward M. Chojin, Boulder, CO (US); Glenn A. Horner, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/571,821

(22) Filed: Aug. 10, 2012

(65) Prior Publication Data

US 2012/0303023 A1    Nov. 29, 2012

Related U.S. Application Data

(63) Continuation of application No. 12/499,553, filed on Jul. 8, 2009, now Pat. No. 8,246,618.

(51) Int. Cl.
*A61B 17/29* (2006.01)
*A61B 18/14* (2006.01)

(52) U.S. Cl.
USPC ................................ 606/205; 606/51; 606/46

(58) Field of Classification Search
USPC ...................... 606/45–52, 205–207
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |

(Continued)

FOREIGN PATENT DOCUMENTS

| | | |
|---|---|---|
| CA | 2104423 A1 | 2/1994 |
| CA | 2520413 A1 | 3/2007 |

(Continued)

OTHER PUBLICATIONS

U.S. Appl. No. 08/926,869, James G. Chandler.

(Continued)

*Primary Examiner* — Michael Peffley

(57) ABSTRACT

A forceps includes an end effector assembly having first and second jaw members. Each jaw member includes a proximal flange having an inwardly-facing surface. The proximal flanges are coupled to one another for moving the jaw members relative to one another between a first position and a second position for grasping tissue therebetween. The inwardly-facing surfaces of the proximal flanges are disposed in abutting relation relative to one another. A knife is configured to move along a knife path defined along an outwardly-facing surface of one of the proximal flanges. The knife is movable between a retracted position and an extended position, wherein the knife extends between the jaw members to cut tissue grasped therebetween.

14 Claims, 11 Drawing Sheets

(56) References Cited

U.S. PATENT DOCUMENTS

| | | |
|---|---|---|
| 2,113,246 A | 5/1937 | Wappler |
| 2,141,936 A | 12/1938 | Schmitt |
| 2,176,479 A | 10/1939 | Willis |
| 2,245,030 A | 6/1941 | Gottesfeld et al. |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 2,824,915 A | 2/1958 | Buturuga |
| 3,073,311 A | 1/1963 | Tibbs et al. |
| 3,100,489 A | 8/1963 | Bagley |
| 3,204,807 A | 9/1965 | Ramsing |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,798,688 A | 3/1974 | Wasson |
| 3,801,766 A | 4/1974 | Morrison, Jr. |
| 3,839,614 A | 10/1974 | Saganowski et al. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,031,898 A | 6/1977 | Hiltebrandt et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,102,471 A | 7/1978 | Lore et al. |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,200,105 A | 4/1980 | Gonser |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | de Medinaceli |
| 4,311,145 A | 1/1982 | Esty et al. |
| D263,020 S | 2/1982 | Rau, III |
| 4,315,510 A | 2/1982 | Kihn |
| 4,363,944 A | 12/1982 | Poirier |
| 4,370,980 A | 2/1983 | Lottick |
| 4,375,218 A | 3/1983 | DiGeronimo |
| 4,394,552 A | 7/1983 | Schlosser |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,535,773 A | 8/1985 | Yoon |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,625,723 A | 12/1986 | Altnether et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,753,235 A | 6/1988 | Hasson |
| 4,754,892 A | 7/1988 | Retief |
| 4,763,669 A | 8/1988 | Jaeger |
| D298,353 S | 11/1988 | Manno |
| 4,781,175 A | 11/1988 | McGreevy et al. |
| D299,413 S | 1/1989 | DeCarolis |
| 4,805,616 A | 2/1989 | Pao |
| 4,827,927 A | 5/1989 | Newton |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |
| 4,973,801 A | 11/1990 | Frick et al. |
| 4,985,030 A | 1/1991 | Melzer et al. |
| 5,007,908 A | 4/1991 | Rydell |
| 5,019,678 A | 5/1991 | Templeton et al. |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,052,402 A | 10/1991 | Bencini et al. |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,144,323 A | 9/1992 | Yonkers |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,169,396 A | 12/1992 | Dowlatshahi et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,231,997 A | 8/1993 | Kikuchi et al. |
| 5,244,462 A | 9/1993 | Delahuerga et al. |
| 5,250,047 A | 10/1993 | Rydell |

| | | |
|---|---|---|
| 5,250,056 A | 10/1993 | Hasson |
| 5,250,063 A | 10/1993 | Abidin et al. |
| 5,254,129 A | 10/1993 | Alexander |
| 5,258,001 A | 11/1993 | Corman |
| 5,258,006 A | 11/1993 | Rydell et al. |
| 5,261,918 A | 11/1993 | Phillips et al. |
| 5,267,998 A | 12/1993 | Hagen |
| 5,269,780 A | 12/1993 | Roos |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,290,287 A | 3/1994 | Boebel et al. |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,312,433 A | 5/1994 | Boebel et al. |
| 5,313,027 A | 5/1994 | Inoue et al. |
| 5,314,445 A | 5/1994 | Heidmueller nee Degwitz et al. |
| 5,314,463 A | 5/1994 | Camps et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,166 A | 8/1994 | Palestrant |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |
| 5,366,477 A | 11/1994 | LeMarie, III et al. |
| 5,367,250 A | 11/1994 | Whisenand |
| 5,368,600 A | 11/1994 | Failla et al. |
| 5,374,277 A | 12/1994 | Hassler |
| 5,376,089 A | 12/1994 | Smith |
| 5,376,094 A | 12/1994 | Kline |
| D354,564 S | 1/1995 | Medema |
| 5,383,875 A | 1/1995 | Bays et al. |
| 5,383,880 A | 1/1995 | Hooven |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,395,360 A | 3/1995 | Manoukian |
| 5,396,194 A | 3/1995 | Williamson et al. |
| 5,396,900 A | 3/1995 | Slater et al. |
| 5,397,325 A | 3/1995 | Della Badia et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,417,709 A | 5/1995 | Slater |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,277 A | 8/1995 | Dumoulin et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,479 A | 8/1995 | Bressi, Jr. |
| 5,443,480 A | 8/1995 | Jacobs et al. |
| 5,445,622 A | 8/1995 | Brown |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,739 A | 10/1995 | Strand |
| 5,454,809 A | 10/1995 | Janssen |
| 5,454,823 A | 10/1995 | Richardson et al. |
| 5,454,827 A | 10/1995 | Aust et al. |
| 5,456,684 A * | 10/1995 | Schmidt et al. ................. 606/41 |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,476,479 A | 12/1995 | Green et al. |
| 5,478,351 A | 12/1995 | Meade et al. |
| 5,480,406 A | 1/1996 | Nolan et al. |
| 5,480,409 A | 1/1996 | Riza |
| 5,482,054 A | 1/1996 | Slater et al. |
| 5,484,436 A | 1/1996 | Eggers et al. |
| 5,493,899 A | 2/1996 | Beck et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,501,654 A | 3/1996 | Failla et al. |
| 5,509,922 A | 4/1996 | Aranyi et al. |
| 5,512,721 A | 4/1996 | Young et al. |
| 5,514,134 A | 5/1996 | Rydell et al. |
| 5,520,702 A | 5/1996 | Sauer et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,549,604 A | 8/1996 | Sutcu et al. |
| 5,554,172 A | 9/1996 | Horner et al. |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,568,859 A | 10/1996 | Levy et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |

| | | | | | | |
|---|---|---|---|---|---|---|
| 5,591,181 A | 1/1997 | Stone et al. | | 5,779,646 A | 7/1998 | Koblish et al. |
| 5,597,107 A | 1/1997 | Knodel et al. | | 5,779,701 A | 7/1998 | McBrayer et al. |
| 5,599,350 A | 2/1997 | Schulze et al. | | 5,779,727 A | 7/1998 | Orejola |
| 5,601,224 A | 2/1997 | Bishop et al. | | 5,781,048 A | 7/1998 | Nakao et al. |
| 5,601,601 A | 2/1997 | Tal et al. | | H1745 H | 8/1998 | Paraschac |
| 5,601,641 A | 2/1997 | Stephens | | 5,791,231 A | 8/1998 | Cohn et al. |
| 5,603,711 A | 2/1997 | Parins et al. | | 5,792,137 A | 8/1998 | Carr et al. |
| 5,603,723 A | 2/1997 | Aranyi et al. | | 5,792,165 A | 8/1998 | Klieman et al. |
| 5,607,436 A | 3/1997 | Pratt et al. | | 5,792,177 A | 8/1998 | Kaseda |
| 5,611,798 A | 3/1997 | Eggers | | 5,797,537 A | 8/1998 | Oberlin et al. |
| 5,611,808 A | 3/1997 | Hossain et al. | | 5,797,927 A | 8/1998 | Yoon |
| 5,611,813 A | 3/1997 | Lichtman | | 5,797,938 A | 8/1998 | Paraschac et al. |
| 5,618,294 A | 4/1997 | Aust et al. | | 5,797,941 A | 8/1998 | Schulze et al. |
| 5,618,307 A | 4/1997 | Donlon et al. | | 5,797,958 A | 8/1998 | Yoon |
| 5,620,415 A | 4/1997 | Lucey et al. | | 5,797,959 A | 8/1998 | Castro et al. |
| 5,620,453 A | 4/1997 | Nallakrishnan | | 5,800,448 A | 9/1998 | Banko |
| 5,620,459 A | 4/1997 | Lichtman | | 5,800,449 A | 9/1998 | Wales |
| 5,624,281 A | 4/1997 | Christensson | | 5,807,393 A | 9/1998 | Williamson, IV et al. |
| 5,624,452 A | 4/1997 | Yates | | 5,810,764 A | 9/1998 | Eggers et al. |
| 5,626,578 A | 5/1997 | Tihon | | 5,810,805 A | 9/1998 | Sutcu et al. |
| 5,626,607 A | 5/1997 | Malecki et al. | | 5,810,808 A | 9/1998 | Eggers |
| 5,626,609 A | 5/1997 | Zvenyatsky et al. | | 5,810,811 A | 9/1998 | Yates et al. |
| 5,630,833 A | 5/1997 | Katsaros et al. | | 5,810,877 A | 9/1998 | Roth et al. |
| 5,637,110 A | 6/1997 | Pennybacker et al. | | 5,814,043 A | 9/1998 | Shapeton |
| 5,637,111 A | 6/1997 | Sutcu et al. | | 5,814,054 A | 9/1998 | Kortenbach et al. |
| 5,638,003 A | 6/1997 | Hall | | 5,817,083 A | 10/1998 | Shemesh et al. |
| 5,638,827 A | 6/1997 | Palmer et al. | | 5,817,119 A | 10/1998 | Klieman et al. |
| 5,639,403 A | 6/1997 | Ida et al. | | 5,820,630 A | 10/1998 | Lind |
| 5,643,294 A | 7/1997 | Tovey et al. | | 5,824,978 A | 10/1998 | Karasik et al. |
| 5,647,869 A | 7/1997 | Goble et al. | | 5,827,271 A | 10/1998 | Buysse et al. |
| 5,647,871 A | 7/1997 | Levine et al. | | 5,827,274 A | 10/1998 | Bonnet et al. |
| 5,649,959 A | 7/1997 | Hannam et al. | | 5,827,279 A | 10/1998 | Hughett et al. |
| 5,655,650 A | 8/1997 | Naitou | | 5,827,281 A | 10/1998 | Levin |
| 5,658,281 A | 8/1997 | Heard | | 5,827,323 A | 10/1998 | Klieman et al. |
| D384,413 S | 9/1997 | Zlock et al. | | 5,827,548 A | 10/1998 | Lavallee et al. |
| 5,662,667 A | 9/1997 | Knodel | | 5,830,212 A | 11/1998 | Cartmell et al. |
| 5,665,100 A | 9/1997 | Yoon | | 5,833,690 A | 11/1998 | Yates et al. |
| 5,667,526 A | 9/1997 | Levin | | 5,833,695 A | 11/1998 | Yoon |
| 5,673,841 A | 10/1997 | Schulze et al. | | 5,836,072 A | 11/1998 | Sullivan et al. |
| 5,674,220 A | 10/1997 | Fox et al. | | D402,028 S | 12/1998 | Grimm et al. |
| 5,674,229 A | 10/1997 | Tovey et al. | | 5,843,080 A | 12/1998 | Fleenor et al. |
| 5,681,282 A | 10/1997 | Eggers et al. | | 5,849,020 A | 12/1998 | Long et al. |
| 5,688,270 A | 11/1997 | Yates et al. | | 5,849,022 A | 12/1998 | Sakashita et al. |
| 5,690,652 A | 11/1997 | Wurster et al. | | 5,851,214 A | 12/1998 | Larsen et al. |
| 5,690,653 A | 11/1997 | Richardson et al. | | 5,853,412 A | 12/1998 | Mayenberger |
| 5,693,051 A | 12/1997 | Schulze et al. | | 5,859,527 A | 1/1999 | Cook |
| 5,693,920 A | 12/1997 | Maeda | | 5,860,976 A | 1/1999 | Billings et al. |
| 5,695,522 A | 12/1997 | LeMaire, III et al. | | 5,865,361 A | 2/1999 | Milliman et al. |
| 5,700,261 A | 12/1997 | Brinkerhoff | | 5,876,401 A | 3/1999 | Schulze et al. |
| 5,700,270 A | 12/1997 | Peyser et al. | | 5,876,410 A | 3/1999 | Petillo |
| 5,702,390 A | 12/1997 | Austin et al. | | 5,876,412 A | 3/1999 | Piraka |
| 5,707,369 A | 1/1998 | Vaitekunas et al. | | 5,882,567 A | 3/1999 | Cavallaro et al. |
| 5,709,680 A | 1/1998 | Yates et al. | | D408,018 S | 4/1999 | McNaughton |
| 5,713,895 A | 2/1998 | Lontine et al. | | 5,891,141 A | 4/1999 | Rydell |
| 5,716,366 A | 2/1998 | Yates | | 5,891,142 A | 4/1999 | Eggers et al. |
| 5,720,742 A | 2/1998 | Zacharias | | 5,893,848 A | 4/1999 | Negus et al. |
| 5,720,744 A | 2/1998 | Eggleston et al. | | 5,893,863 A | 4/1999 | Yoon |
| 5,722,421 A | 3/1998 | Francese et al. | | 5,893,875 A | 4/1999 | O'Connor et al. |
| 5,725,536 A | 3/1998 | Oberlin et al. | | 5,893,877 A | 4/1999 | Gampp, Jr. et al. |
| 5,727,428 A | 3/1998 | LeMaire, III et al. | | 5,897,563 A | 4/1999 | Yoon et al. |
| 5,735,848 A | 4/1998 | Yates et al. | | 5,902,301 A | 5/1999 | Olig |
| 5,735,849 A | 4/1998 | Baden et al. | | 5,906,630 A | 5/1999 | Anderhub et al. |
| 5,743,906 A | 4/1998 | Parins et al. | | 5,907,140 A | 5/1999 | Smith |
| 5,752,973 A | 5/1998 | Kieturakis | | 5,908,420 A | 6/1999 | Parins et al. |
| 5,755,717 A | 5/1998 | Yates et al. | | 5,908,432 A | 6/1999 | Pan |
| 5,759,188 A | 6/1998 | Yoon | | 5,911,719 A | 6/1999 | Eggers |
| 5,762,255 A | 6/1998 | Chrisman et al. | | 5,913,874 A | 6/1999 | Berns et al. |
| 5,762,609 A | 6/1998 | Benaron et al. | | 5,921,916 A | 7/1999 | Aeikens et al. |
| 5,766,130 A | 6/1998 | Selmonosky | | 5,921,984 A | 7/1999 | Sutcu et al. |
| 5,766,166 A | 6/1998 | Hooven | | 5,925,043 A | 7/1999 | Kumar et al. |
| 5,766,170 A | 6/1998 | Eggers | | 5,928,136 A | 7/1999 | Barry |
| 5,766,196 A | 6/1998 | Griffiths | | 5,935,126 A | 8/1999 | Riza |
| 5,769,849 A | 6/1998 | Eggers | | 5,938,589 A | 8/1999 | Wako et al. |
| 5,772,655 A | 6/1998 | Bauer et al. | | 5,941,869 A | 8/1999 | Patterson et al. |
| 5,772,670 A | 6/1998 | Brosa | | 5,944,562 A | 8/1999 | Christensson |
| 5,776,128 A | 7/1998 | Eggers | | 5,944,718 A | 8/1999 | Austin et al. |
| 5,776,130 A | 7/1998 | Buysse et al. | | 5,951,545 A | 9/1999 | Schilling et al. |
| 5,776,156 A | 7/1998 | Shikhman | | 5,951,546 A | 9/1999 | Lorentzen |
| 5,777,519 A | 7/1998 | Simopoulos | | 5,951,549 A | 9/1999 | Richardson et al. |

| | | | | | | |
|---|---|---|---|---|---|---|
| 5,954,720 | A | 9/1999 | Wilson et al. | 6,174,309 B1 | 1/2001 | Wrublewski et al. |
| 5,954,731 | A | 9/1999 | Yoon | 6,174,310 B1 | 1/2001 | Kirwan, Jr. |
| 5,954,733 | A | 9/1999 | Yoon | 6,178,628 B1 | 1/2001 | Clemens et al. |
| 5,957,923 | A | 9/1999 | Hahnen et al. | 6,179,834 B1 | 1/2001 | Buysse et al. |
| 5,957,937 | A | 9/1999 | Yoon | 6,179,837 B1 | 1/2001 | Hooven |
| 5,960,544 | A | 10/1999 | Beyers | 6,183,467 B1 | 2/2001 | Shapeton et al. |
| 5,961,514 | A | 10/1999 | Long et al. | 6,187,003 B1 | 2/2001 | Buysse et al. |
| 5,964,758 | A | 10/1999 | Dresden | 6,190,386 B1 | 2/2001 | Rydell |
| 5,967,997 | A | 10/1999 | Turturro et al. | 6,190,399 B1 | 2/2001 | Palmer et al. |
| D416,089 | S | 11/1999 | Barton et al. | 6,190,400 B1 | 2/2001 | Van De Moer et al. |
| 5,976,132 | A | 11/1999 | Morris | 6,193,709 B1 | 2/2001 | Miyawaki et al. |
| 5,984,932 | A | 11/1999 | Yoon | 6,193,718 B1 | 2/2001 | Kortenbach et al. |
| 5,984,938 | A | 11/1999 | Yoon | 6,206,876 B1 | 3/2001 | Levine et al. |
| 5,984,939 | A | 11/1999 | Yoon | 6,206,877 B1 | 3/2001 | Kese et al. |
| 5,989,277 | A | 11/1999 | LeMaire, III et al. | 6,206,893 B1 | 3/2001 | Klein et al. |
| 5,993,466 | A | 11/1999 | Yoon | 6,214,028 B1 | 4/2001 | Yoon et al. |
| 5,993,467 | A | 11/1999 | Yoon | 6,217,602 B1 | 4/2001 | Redmon |
| 5,993,474 | A | 11/1999 | Ouchi | 6,217,615 B1 | 4/2001 | Sioshansi et al. |
| 5,997,565 | A | 12/1999 | Inoue | 6,221,039 B1 | 4/2001 | Durgin et al. |
| 6,003,517 | A | 12/1999 | Sheffield et al. | 6,223,100 B1 | 4/2001 | Green |
| 6,004,332 | A | 12/1999 | Yoon et al. | 6,224,593 B1 | 5/2001 | Ryan et al. |
| 6,004,335 | A | 12/1999 | Vaitekunas et al. | 6,224,614 B1 | 5/2001 | Yoon |
| 6,010,516 | A | 1/2000 | Hulka | 6,228,080 B1 | 5/2001 | Gines |
| 6,010,519 | A | 1/2000 | Mawhirt et al. | 6,228,083 B1 | 5/2001 | Lands et al. |
| 6,017,354 | A | 1/2000 | Culp et al. | 6,248,124 B1 | 6/2001 | Pedros et al. |
| 6,017,358 | A | 1/2000 | Yoon et al. | 6,248,944 B1 | 6/2001 | Ito |
| 6,021,693 | A | 2/2000 | Feng-Sing | 6,249,706 B1 | 6/2001 | Sobota et al. |
| 6,024,741 | A | 2/2000 | Williamson, IV et al. | 6,261,307 B1 | 7/2001 | Yoon et al. |
| 6,024,743 | A | 2/2000 | Edwards | 6,267,758 B1 | 7/2001 | Daw et al. |
| 6,024,744 | A | 2/2000 | Kese et al. | 6,267,761 B1 | 7/2001 | Ryan |
| 6,027,522 | A | 2/2000 | Palmer | 6,270,497 B1 | 8/2001 | Sekino et al. |
| 6,030,384 | A | 2/2000 | Nezhat | 6,270,508 B1 | 8/2001 | Klieman et al. |
| 6,033,399 | A | 3/2000 | Gines | 6,273,887 B1 | 8/2001 | Yamauchi et al. |
| 6,039,733 | A | 3/2000 | Buysse et al. | 6,277,117 B1 | 8/2001 | Tetzlaff et al. |
| 6,041,679 | A | 3/2000 | Slater et al. | 6,280,458 B1 | 8/2001 | Boche et al. |
| 6,050,995 | A | 4/2000 | Durgin | 6,283,961 B1 | 9/2001 | Underwood et al. |
| 6,050,996 | A | 4/2000 | Schmaltz et al. | D449,886 S | 10/2001 | Tetzlaff et al. |
| 6,053,914 | A | 4/2000 | Eggers et al. | 6,298,550 B1 | 10/2001 | Kirwan, Jr. |
| 6,053,933 | A | 4/2000 | Balazs et al. | 6,302,424 B1 | 10/2001 | Gisinger et al. |
| D424,694 | S | 5/2000 | Tetzlaff et al. | 6,303,166 B1 | 10/2001 | Kolbe et al. |
| D425,201 | S | 5/2000 | Tetzlaff et al. | 6,309,404 B1 | 10/2001 | Krzyzanowski |
| 6,056,735 | A | 5/2000 | Okada et al. | 6,319,262 B1 | 11/2001 | Bates et al. |
| 6,059,782 | A | 5/2000 | Novak et al. | 6,319,451 B1 | 11/2001 | Brune |
| 6,063,086 | A | 5/2000 | Benecke et al. | 6,322,561 B1 | 11/2001 | Eggers et al. |
| 6,063,103 | A | 5/2000 | Hashiguchi | 6,322,580 B1 | 11/2001 | Kanner |
| 6,066,137 | A | 5/2000 | Greep | 6,325,795 B1 | 12/2001 | Lindemann et al. |
| 6,066,139 | A | 5/2000 | Ryan et al. | 6,329,778 B1 | 12/2001 | Culp et al. |
| 6,071,283 | A | 6/2000 | Nardella et al. | 6,334,860 B1 | 1/2002 | Dorn |
| 6,074,386 | A | 6/2000 | Goble et al. | 6,334,861 B1 | 1/2002 | Chandler et al. |
| 6,077,287 | A | 6/2000 | Taylor et al. | D453,923 S | 2/2002 | Olson |
| 6,080,180 | A | 6/2000 | Yoon et al. | 6,345,532 B1 | 2/2002 | Coudray et al. |
| RE36,795 | E | 7/2000 | Rydell | 6,350,264 B1 | 2/2002 | Hooven |
| 6,083,150 | A | 7/2000 | Aznoian et al. | D454,951 S | 3/2002 | Bon |
| 6,083,223 | A | 7/2000 | Baker | 6,352,536 B1 | 3/2002 | Buysse et al. |
| 6,086,586 | A | 7/2000 | Hooven | 6,358,249 B1 | 3/2002 | Chen et al. |
| 6,086,601 | A | 7/2000 | Yoon | 6,358,259 B1 | 3/2002 | Swain et al. |
| 6,090,107 | A | 7/2000 | Borgmeier et al. | 6,358,268 B1 | 3/2002 | Hunt et al. |
| 6,090,123 | A | 7/2000 | Culp et al. | 6,361,534 B1 | 3/2002 | Chen et al. |
| 6,096,037 | A | 8/2000 | Mulier et al. | 6,364,876 B1 | 4/2002 | Erb et al. |
| 6,099,537 | A | 8/2000 | Sugai et al. | 6,364,879 B1 | 4/2002 | Chen et al. |
| 6,099,550 | A | 8/2000 | Yoon | D457,958 S | 5/2002 | Dycus et al. |
| 6,102,909 | A | 8/2000 | Chen et al. | D457,959 S | 5/2002 | Tetzlaff et al. |
| 6,106,542 | A | 8/2000 | Toybin et al. | 6,385,265 B1 | 5/2002 | Duffy et al. |
| 6,110,171 | A | 8/2000 | Rydell | 6,387,094 B1 | 5/2002 | Eitenmuller |
| 6,113,596 | A | 9/2000 | Hooven et al. | 6,391,035 B1 | 5/2002 | Appleby et al. |
| 6,113,598 | A | 9/2000 | Baker | 6,398,779 B1 | 6/2002 | Buysse et al. |
| 6,117,158 | A | 9/2000 | Measamer et al. | 6,402,747 B1 | 6/2002 | Lindemann et al. |
| 6,122,549 | A | 9/2000 | Sharkey et al. | 6,409,728 B1 | 6/2002 | Ehr et al. |
| 6,123,701 | A | 9/2000 | Nezhat | H2037 H | 7/2002 | Yates et al. |
| H1904 | H | 10/2000 | Yates et al. | 6,419,675 B1 | 7/2002 | Gallo, Sr. |
| 6,126,658 | A | 10/2000 | Baker | 6,425,896 B1 | 7/2002 | Baltschun et al. |
| 6,126,665 | A | 10/2000 | Yoon | 6,432,112 B2 | 8/2002 | Brock et al. |
| 6,139,563 | A | 10/2000 | Cosgrove, III et al. | 6,440,130 B1 | 8/2002 | Mulier et al. |
| 6,143,005 | A | 11/2000 | Yoon et al. | 6,440,144 B1 | 8/2002 | Bacher |
| 6,152,923 | A | 11/2000 | Ryan | 6,443,952 B1 | 9/2002 | Mulier et al. |
| 6,152,924 | A | 11/2000 | Parins | 6,443,970 B1 | 9/2002 | Schulze et al. |
| 6,159,217 | A | 12/2000 | Robie et al. | 6,451,018 B1 | 9/2002 | Lands et al. |
| 6,162,220 | A | 12/2000 | Nezhat | 6,458,125 B1 | 10/2002 | Cosmescu |
| 6,171,316 | B1 | 1/2001 | Kovac et al. | 6,458,128 B1 | 10/2002 | Schulze |

| Patent No. | Date | Inventor |
|---|---|---|
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,882 B1 | 12/2002 | Lebouitz et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,536 B2 | 2/2003 | Hooven et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,537,272 B2 | 3/2003 | Christopherson et al. |
| 6,540,745 B1 | 4/2003 | Fairbourn et al. |
| 6,545,239 B2 | 4/2003 | Spedale et al. |
| 6,554,829 B2 | 4/2003 | Schulze et al. |
| 6,554,844 B2 | 4/2003 | Lee et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,610,060 B2 | 8/2003 | Mulier et al. |
| 6,613,048 B2 | 9/2003 | Mulier et al. |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,623,482 B2 | 9/2003 | Pendekanti et al. |
| 6,626,901 B1 | 9/2003 | Treat et al. |
| 6,629,534 B1 | 10/2003 | St. Goar et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,518 B2 | 11/2003 | Wellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,666,862 B2 | 12/2003 | Jain et al. |
| 6,669,696 B2 | 12/2003 | Bacher et al. |
| 6,673,092 B1 | 1/2004 | Bacher |
| 6,676,660 B1 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,704 B2 | 2/2004 | Greep |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,709,445 B2 | 3/2004 | Boebel et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,824 B2 | 6/2004 | Jain et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| 6,758,846 B2 | 7/2004 | Goble et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,435 B2 | 8/2004 | Schulze et al. |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,780,181 B2 | 8/2004 | Kroll et al. |
| 6,784,405 B2 | 8/2004 | Flugstad et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,273 B2 | 11/2004 | Mollenauer |
| 6,821,285 B2 | 11/2004 | Laufer et al. |
| 6,824,547 B2 | 11/2004 | Wilson, Jr. et al. |
| 6,830,174 B2 | 12/2004 | Hillstead et al. |
| 6,835,200 B2 | 12/2004 | Laufer et al. |
| 6,843,789 B2 | 1/2005 | Goble |
| 6,857,357 B2 | 2/2005 | Fujii |
| 6,858,028 B2 | 2/2005 | Mulier et al. |
| D502,994 S | 3/2005 | Blake, III |
| 6,860,880 B2 | 3/2005 | Treat et al. |
| 6,878,147 B2 | 4/2005 | Prakash et al. |
| 6,887,240 B1 | 5/2005 | Lands et al. |
| 6,889,116 B2 | 5/2005 | Jinno |
| 6,905,497 B2 | 6/2005 | Truckai et al. |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,974,452 B2 | 12/2005 | Gille et al. |
| 6,976,492 B2 | 12/2005 | Ingle et al. |
| 6,976,992 B2 | 12/2005 | Sachatello et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,989,010 B2 | 1/2006 | Francischelli et al. |
| 6,989,017 B2 | 1/2006 | Howell et al. |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |

| Patent | Type | Date | Inventor |
|---|---|---|---|
| 7,001,408 | B2 | 2/2006 | Knodel et al. |
| 7,011,657 | B2 | 3/2006 | Truckai et al. |
| 7,025,763 | B2 | 4/2006 | Karasawa et al. |
| 7,033,354 | B2 | 4/2006 | Keppel |
| 7,033,356 | B2 | 4/2006 | Latterell et al. |
| 7,041,102 | B2 | 5/2006 | Truckai et al. |
| 7,044,948 | B2 | 5/2006 | Keppel |
| 7,052,489 | B2 | 5/2006 | Griego et al. |
| 7,052,496 | B2 | 5/2006 | Yamauchi |
| 7,063,699 | B2 | 6/2006 | Hess et al. |
| 7,063,715 | B2 | 6/2006 | Onuki et al. |
| D525,361 | S | 7/2006 | Hushka |
| 7,070,597 | B2 | 7/2006 | Truckai et al. |
| 7,083,480 | B2 | 8/2006 | Silber |
| 7,083,618 | B2 | 8/2006 | Couture et al. |
| 7,083,619 | B2 | 8/2006 | Truckai et al. |
| 7,083,620 | B2 | 8/2006 | Jahns et al. |
| 7,087,051 | B2 | 8/2006 | Bourne et al. |
| 7,087,054 | B2 | 8/2006 | Truckai et al. |
| 7,090,673 | B2 | 8/2006 | Dycus et al. |
| 7,090,689 | B2 | 8/2006 | Nagase et al. |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,103,947 | B2 | 9/2006 | Sartor et al. |
| 7,107,124 | B2 | 9/2006 | Green |
| 7,108,694 | B2 | 9/2006 | Miura et al. |
| 7,112,199 | B2 | 9/2006 | Cosmescu |
| 7,112,201 | B2 | 9/2006 | Truckai et al. |
| D531,311 | S | 10/2006 | Guerra et al. |
| 7,115,123 | B2 | 10/2006 | Knowlton et al. |
| 7,115,139 | B2 | 10/2006 | McClurken et al. |
| 7,118,570 | B2 | 10/2006 | Tetzlaff et al. |
| 7,118,587 | B2 | 10/2006 | Dycus et al. |
| 7,131,860 | B2 | 11/2006 | Sartor et al. |
| 7,131,970 | B2 * | 11/2006 | Moses et al. .................. 606/51 |
| 7,131,971 | B2 | 11/2006 | Dycus et al. |
| 7,135,018 | B2 | 11/2006 | Ryan et al. |
| 7,135,020 | B2 | 11/2006 | Lawes et al. |
| 7,137,980 | B2 | 11/2006 | Buysse et al. |
| D533,274 | S | 12/2006 | Visconti et al. |
| D533,942 | S | 12/2006 | Kerr et al. |
| 7,145,757 | B2 | 12/2006 | Shea et al. |
| 7,147,632 | B2 | 12/2006 | Prakash et al. |
| 7,147,638 | B2 | 12/2006 | Chapman et al. |
| 7,150,097 | B2 | 12/2006 | Sremcich et al. |
| 7,150,749 | B2 | 12/2006 | Dycus et al. |
| 7,153,314 | B2 | 12/2006 | Laufer et al. |
| D535,027 | S | 1/2007 | James et al. |
| 7,156,842 | B2 | 1/2007 | Sartor et al. |
| 7,156,846 | B2 | 1/2007 | Dycus et al. |
| 7,160,298 | B2 | 1/2007 | Lawes et al. |
| 7,160,299 | B2 | 1/2007 | Baily |
| 7,166,106 | B2 | 1/2007 | Bartel et al. |
| 7,169,145 | B2 | 1/2007 | Isaacson et al. |
| 7,169,146 | B2 | 1/2007 | Truckai et al. |
| 7,179,255 | B2 | 2/2007 | Lettice et al. |
| 7,179,258 | B2 | 2/2007 | Buysse et al. |
| 7,184,820 | B2 | 2/2007 | Jersey-Willuhn et al. |
| D538,932 | S | 3/2007 | Malik |
| 7,189,233 | B2 | 3/2007 | Truckai et al. |
| 7,195,631 | B2 | 3/2007 | Dumbauld |
| D541,418 | S | 4/2007 | Schechter et al. |
| 7,204,832 | B2 | 4/2007 | Altshuler et al. |
| 7,204,835 | B2 | 4/2007 | Latterell et al. |
| 7,207,990 | B2 | 4/2007 | Lands et al. |
| 7,208,005 | B2 | 4/2007 | Frecker et al. |
| D541,611 | S | 5/2007 | Aglassinge |
| D541,938 | S | 5/2007 | Kerr et al. |
| 7,211,084 | B2 | 5/2007 | Goble et al. |
| 7,223,264 | B2 | 5/2007 | Daniel et al. |
| 7,223,265 | B2 | 5/2007 | Keppel |
| D545,432 | S | 6/2007 | Watanabe |
| 7,232,440 | B2 | 6/2007 | Dumbauld et al. |
| D547,154 | S | 7/2007 | Lee |
| 7,238,184 | B2 | 7/2007 | Megerman et al. |
| 7,241,288 | B2 | 7/2007 | Braun |
| 7,241,296 | B2 | 7/2007 | Buysse et al. |
| 7,244,257 | B2 | 7/2007 | Podhajsky et al. |
| 7,246,734 | B2 | 7/2007 | Shelton, IV |
| 7,248,944 | B2 | 7/2007 | Green |
| 7,252,667 | B2 | 8/2007 | Moses et al. |
| 7,254,433 | B2 | 8/2007 | Diab et al. |
| 7,255,697 | B2 | 8/2007 | Dycus et al. |
| 7,258,688 | B1 | 8/2007 | Shah et al. |
| 7,267,677 | B2 | 9/2007 | Johnson et al. |
| 7,270,660 | B2 | 9/2007 | Ryan |
| 7,270,664 | B2 | 9/2007 | Johnson et al. |
| 7,276,068 | B2 | 10/2007 | Johnson et al. |
| 7,288,103 | B2 | 10/2007 | Suzuki |
| 7,291,161 | B2 | 11/2007 | Hooven |
| 7,300,435 | B2 | 11/2007 | Wham et al. |
| 7,303,557 | B2 | 12/2007 | Wham et al. |
| 7,311,709 | B2 | 12/2007 | Truckai et al. |
| 7,314,471 | B2 | 1/2008 | Holman |
| 7,318,823 | B2 | 1/2008 | Sharps et al. |
| 7,326,202 | B2 | 2/2008 | McGaffigan |
| 7,329,256 | B2 | 2/2008 | Johnson et al. |
| 7,329,257 | B2 | 2/2008 | Kanehira et al. |
| D564,662 | S | 3/2008 | Moses et al. |
| 7,338,526 | B2 | 3/2008 | Steinberg |
| 7,342,754 | B2 | 3/2008 | Fitzgerald et al. |
| 7,344,268 | B2 | 3/2008 | Jigamian |
| 7,347,864 | B2 | 3/2008 | Vargas |
| D567,943 | S | 4/2008 | Moses et al. |
| 7,354,440 | B2 | 4/2008 | Truckai et al. |
| 7,361,172 | B2 | 4/2008 | Cimino |
| 7,367,976 | B2 | 5/2008 | Lawes et al. |
| 7,377,920 | B2 | 5/2008 | Buysse et al. |
| 7,384,420 | B2 | 6/2008 | Dycus et al. |
| 7,384,421 | B2 | 6/2008 | Hushka |
| 7,396,265 | B2 | 7/2008 | Darley et al. |
| 7,396,336 | B2 | 7/2008 | Orszulak et al. |
| 7,396,356 | B2 | 7/2008 | Mollenauer |
| D575,395 | S | 8/2008 | Hushka |
| D575,401 | S | 8/2008 | Hixson et al. |
| 7,422,592 | B2 | 9/2008 | Morley et al. |
| 7,425,835 | B2 | 9/2008 | Eisele |
| 7,431,721 | B2 | 10/2008 | Paton et al. |
| 7,435,249 | B2 | 10/2008 | Buysse et al. |
| 7,438,714 | B2 | 10/2008 | Phan |
| 7,442,193 | B2 | 10/2008 | Shields et al. |
| 7,442,194 | B2 | 10/2008 | Dumbauld et al. |
| 7,445,621 | B2 | 11/2008 | Dumbauld et al. |
| D582,038 | S | 12/2008 | Swoyer et al. |
| 7,458,972 | B2 | 12/2008 | Keppel |
| 7,473,253 | B2 | 1/2009 | Dycus et al. |
| 7,481,810 | B2 | 1/2009 | Dumbauld et al. |
| 7,487,780 | B2 | 2/2009 | Hooven |
| 7,491,201 | B2 | 2/2009 | Shields et al. |
| 7,491,202 | B2 | 2/2009 | Odom et al. |
| 7,500,975 | B2 | 3/2009 | Cunningham et al. |
| 7,503,474 | B2 | 3/2009 | Hillstead et al. |
| 7,510,556 | B2 | 3/2009 | Nguyen et al. |
| 7,513,898 | B2 | 4/2009 | Johnson et al. |
| 7,517,351 | B2 | 4/2009 | Culp et al. |
| 7,540,872 | B2 | 6/2009 | Schechter et al. |
| 7,549,995 | B2 | 6/2009 | Schultz |
| 7,553,312 | B2 | 6/2009 | Tetzlaff et al. |
| 7,553,686 | B2 | 6/2009 | George et al. |
| 7,569,626 | B2 | 8/2009 | Truckai |
| 7,582,087 | B2 | 9/2009 | Tetzlaff et al. |
| 7,588,565 | B2 | 9/2009 | Marchitto et al. |
| 7,594,313 | B2 | 9/2009 | Prakash et al. |
| 7,594,916 | B2 | 9/2009 | Weinberg |
| 7,597,693 | B2 | 10/2009 | Garrison |
| 7,621,910 | B2 | 11/2009 | Sugi |
| 7,624,186 | B2 | 11/2009 | Tanida |
| 7,625,370 | B2 | 12/2009 | Hart et al. |
| 7,628,791 | B2 | 12/2009 | Garrison et al. |
| 7,628,792 | B2 | 12/2009 | Guerra |
| 7,637,409 | B2 | 12/2009 | Marczyk |
| 7,641,653 | B2 | 1/2010 | Dalla Betta et al. |
| 7,651,493 | B2 | 1/2010 | Arts et al. |
| 7,651,494 | B2 | 1/2010 | McClurken et al. |
| 7,655,004 | B2 | 2/2010 | Long |
| 7,655,007 | B2 | 2/2010 | Baily |
| 7,668,597 | B2 | 2/2010 | Engmark et al. |

| Patent No. | Date | Inventor |
|---|---|---|
| 7,678,111 B2 | 3/2010 | Mulier et al. |
| 7,686,804 B2 | 3/2010 | Johnson et al. |
| 7,686,827 B2 | 3/2010 | Hushka |
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,717,914 B2 | 5/2010 | Kimura |
| 7,717,915 B2 | 5/2010 | Miyazawa |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,727,231 B2 | 6/2010 | Swanson |
| 7,731,717 B2 | 6/2010 | Odom et al. |
| 7,736,374 B2 | 6/2010 | Vaughan et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |
| 7,780,662 B2 | 8/2010 | Bahney |
| 7,780,663 B2 | 8/2010 | Yates et al. |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,806,892 B2 | 10/2010 | Makin et al. |
| 7,811,283 B2 | 10/2010 | Moses et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| 7,832,408 B2 | 11/2010 | Shelton, IV et al. |
| 7,837,685 B2 | 11/2010 | Weinberg et al. |
| 7,839,674 B2 | 11/2010 | Lowrey et al. |
| 7,842,033 B2 | 11/2010 | Isaacson et al. |
| 7,846,158 B2 | 12/2010 | Podhajsky |
| 7,846,161 B2 | 12/2010 | Dumbauld et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,535 B2 | 2/2011 | Lands et al. |
| 7,887,536 B2 | 2/2011 | Johnson et al. |
| 7,896,878 B2 | 3/2011 | Johnson et al. |
| 7,898,288 B2 | 3/2011 | Wong |
| 7,900,805 B2 | 3/2011 | Shelton, IV et al. |
| 7,901,400 B2 | 3/2011 | Wham et al. |
| 7,905,380 B2 | 3/2011 | Shelton, IV et al. |
| 7,905,881 B2 | 3/2011 | Masuda et al. |
| 7,909,820 B2 | 3/2011 | Lipson et al. |
| 7,909,823 B2 | 3/2011 | Moses et al. |
| 7,909,824 B2 | 3/2011 | Masuda et al. |
| 7,918,848 B2 | 4/2011 | Lau et al. |
| 7,922,718 B2 | 4/2011 | Moses et al. |
| 7,922,742 B2 | 4/2011 | Hillstead et al. |
| 7,922,953 B2 | 4/2011 | Guerra |
| 7,931,649 B2 | 4/2011 | Couture et al. |
| 7,935,052 B2 | 5/2011 | Dumbauld |
| 7,945,332 B2 | 5/2011 | Schechter |
| 7,947,041 B2 | 5/2011 | Tetzlaff et al. |
| 7,949,407 B2 | 5/2011 | Kaplan et al. |
| 7,951,149 B2 | 5/2011 | Carlton |
| 7,951,150 B2 | 5/2011 | Johnson et al. |
| 7,955,326 B2 | 6/2011 | Paul et al. |
| 7,955,327 B2 | 6/2011 | Sartor et al. |
| 7,955,331 B2 | 6/2011 | Truckai et al. |
| 7,955,332 B2 | 6/2011 | Arts et al. |
| 7,963,965 B2 | 6/2011 | Buysse et al. |
| 7,967,839 B2 | 6/2011 | Flock et al. |
| 7,972,328 B2 | 7/2011 | Wham et al. |
| 7,972,331 B2 | 7/2011 | Hafner |
| 7,976,544 B2 | 7/2011 | McClurken et al. |
| 7,981,113 B2 | 7/2011 | Truckai et al. |
| 7,988,507 B2 | 8/2011 | Darley et al. |
| 7,998,095 B2 | 8/2011 | McAuley |
| 8,012,150 B2 | 9/2011 | Wham et al. |
| 8,016,827 B2 | 9/2011 | Chojin |
| 8,034,049 B2 | 10/2011 | Odom et al. |
| D649,249 S | 11/2011 | Guerra |
| D649,643 S | 11/2011 | Allen, IV et al. |
| 8,048,074 B2 | 11/2011 | Masuda |
| 8,070,746 B2 | 12/2011 | Orton et al. |
| 8,070,748 B2 | 12/2011 | Hixson et al. |
| 8,075,580 B2 | 12/2011 | Makower |
| 8,089,417 B2 | 1/2012 | Popovic et al. |
| 8,092,451 B2 | 1/2012 | Schechter et al. |
| 8,104,956 B2 | 1/2012 | Blaha |
| 8,112,871 B2 | 2/2012 | Brandt et al. |
| 8,114,122 B2 | 2/2012 | Nau, Jr. |
| 8,123,743 B2 | 2/2012 | Arts et al. |
| 8,128,624 B2 | 3/2012 | Couture et al. |
| 8,128,625 B2 | 3/2012 | Odom |
| 8,133,224 B2 | 3/2012 | Geiselhart |
| 8,133,254 B2 | 3/2012 | Dumbauld et al. |
| 8,142,425 B2 | 3/2012 | Eggers |
| 8,142,473 B2 | 3/2012 | Cunningham |
| 8,147,485 B2 | 4/2012 | Wham et al. |
| 8,147,489 B2 | 4/2012 | Moses et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,162,965 B2 | 4/2012 | Reschke et al. |
| 8,162,973 B2 | 4/2012 | Cunningham |
| 8,177,794 B2 | 5/2012 | Cabrera et al. |
| 8,181,649 B2 | 5/2012 | Brunner |
| 8,182,476 B2 | 5/2012 | Julian et al. |
| 8,187,273 B2 | 5/2012 | Kerr et al. |
| D661,394 S | 6/2012 | Romero et al. |
| 8,192,433 B2 | 6/2012 | Johnson et al. |
| 8,192,444 B2 | 6/2012 | Dycus |
| 8,197,479 B2 | 6/2012 | Olson et al. |
| 8,197,633 B2 | 6/2012 | Guerra |
| 8,207,651 B2 | 6/2012 | Gilbert |
| 8,211,105 B2 | 7/2012 | Buysse et al. |
| 8,215,182 B2 | 7/2012 | Artale et al. |
| 8,216,223 B2 | 7/2012 | Wham et al. |
| 8,221,416 B2 | 7/2012 | Townsend |
| 8,226,650 B2 | 7/2012 | Kerr |
| 8,235,992 B2 | 8/2012 | Guerra et al. |
| 8,235,993 B2 | 8/2012 | Hushka et al. |
| 8,236,025 B2 | 8/2012 | Hushka et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,246,618 B2 * | 8/2012 | Bucciaglia et al. ............. 606/51 |
| 8,251,994 B2 | 8/2012 | Mckenna et al. |
| 8,251,996 B2 | 8/2012 | Hushka et al. |
| 8,257,352 B2 | 9/2012 | Lawes et al. |
| 8,257,387 B2 | 9/2012 | Cunningham |
| 2002/0029036 A1 | 3/2002 | Goble et al. |
| 2002/0107517 A1 | 8/2002 | Witt et al. |
| 2002/0111624 A1 | 8/2002 | Witt et al. |
| 2002/0165469 A1 | 11/2002 | Murakami |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0181910 A1 | 9/2003 | Dycus et al. |
| 2003/0191396 A1 | 10/2003 | Sanghvi et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |

| | | | | | |
|---|---|---|---|---|---|
| 2004/0064151 A1 | 4/2004 | Mollenauer | 2009/0088745 A1 | 4/2009 | Hushka et al. |
| 2004/0115296 A1 | 6/2004 | Duffin | 2009/0088746 A1 | 4/2009 | Hushka et al. |
| 2004/0176779 A1 | 9/2004 | Casutt et al. | 2009/0088748 A1 | 4/2009 | Guerra et al. |
| 2004/0199181 A1 | 10/2004 | Knodel et al. | 2009/0088750 A1 | 4/2009 | Hushka et al. |
| 2004/0224590 A1 | 11/2004 | Rawa et al. | 2009/0105750 A1 | 4/2009 | Price et al. |
| 2004/0236326 A1 | 11/2004 | Schulze et al. | 2009/0112206 A1 | 4/2009 | Dumbauld et al. |
| 2004/0249374 A1 | 12/2004 | Tetzlaff et al. | 2009/0112229 A1 | 4/2009 | Omori et al. |
| 2004/0260281 A1 | 12/2004 | Baxter et al. | 2009/0131934 A1 | 5/2009 | Odom et al. |
| 2005/0004569 A1 | 1/2005 | Witt et al. | 2009/0138003 A1 | 5/2009 | Deville et al. |
| 2005/0033278 A1 | 2/2005 | McClurken et al. | 2009/0138006 A1 | 5/2009 | Bales et al. |
| 2005/0059858 A1 | 3/2005 | Frith et al. | 2009/0149853 A1 | 6/2009 | Shields et al. |
| 2005/0059934 A1 | 3/2005 | Wenchell et al. | 2009/0149854 A1 | 6/2009 | Cunningham et al. |
| 2005/0090817 A1 | 4/2005 | Phan | 2009/0157071 A1 | 6/2009 | Wham et al. |
| 2005/0096645 A1 | 5/2005 | Wellman et al. | 2009/0171354 A1 | 7/2009 | Deville et al. |
| 2005/0149017 A1 | 7/2005 | Dycus | 2009/0177094 A1 | 7/2009 | Brown et al. |
| 2005/0222560 A1 | 10/2005 | Kimura et al. | 2009/0182327 A1 | 7/2009 | Unger |
| 2005/0254081 A1 | 11/2005 | Ryu et al. | 2009/0187188 A1 | 7/2009 | Guerra et al. |
| 2005/0261588 A1 | 11/2005 | Makin et al. | 2009/0198233 A1 | 8/2009 | Chojin |
| 2005/0283148 A1 | 12/2005 | Janssen et al. | 2009/0204114 A1 | 8/2009 | Odom |
| 2006/0052779 A1 | 3/2006 | Hammill | 2009/0204137 A1 | 8/2009 | Maxwell |
| 2006/0064086 A1 | 3/2006 | Odom | 2009/0206126 A1 | 8/2009 | Huitema et al. |
| 2006/0079891 A1* | 4/2006 | Arts et al. ............ 606/51 | 2009/0209957 A1 | 8/2009 | Schmaltz et al. |
| 2006/0079933 A1 | 4/2006 | Hushka et al. | 2009/0209960 A1 | 8/2009 | Chojin |
| 2006/0084973 A1 | 4/2006 | Hushka | 2009/0234354 A1 | 9/2009 | Johnson et al. |
| 2006/0111711 A1 | 5/2006 | Goble | 2009/0248007 A1 | 10/2009 | Falkenstein et al. |
| 2006/0173452 A1 | 8/2006 | Buysse et al. | 2009/0248013 A1 | 10/2009 | Falkenstein et al. |
| 2006/0190035 A1 | 8/2006 | Hushka et al. | 2009/0248019 A1 | 10/2009 | Falkenstein et al. |
| 2006/0224053 A1 | 10/2006 | Black et al. | 2009/0248020 A1 | 10/2009 | Falkenstein et al. |
| 2006/0253126 A1 | 11/2006 | Bjerken et al. | 2009/0248021 A1 | 10/2009 | Mckenna |
| 2006/0259036 A1 | 11/2006 | Tetzlaff et al. | 2009/0248022 A1 | 10/2009 | Falkenstein et al. |
| 2006/0264922 A1 | 11/2006 | Sartor et al. | 2009/0248050 A1 | 10/2009 | Hirai |
| 2006/0271030 A1 | 11/2006 | Francis et al. | 2009/0254080 A1 | 10/2009 | Honda |
| 2006/0283093 A1 | 12/2006 | Petrovic et al. | 2009/0254081 A1 | 10/2009 | Allison et al. |
| 2006/0287641 A1 | 12/2006 | Perlin | 2009/0261804 A1 | 10/2009 | Mckenna et al. |
| 2007/0027447 A1 | 2/2007 | Theroux et al. | 2009/0270771 A1 | 10/2009 | Takahashi |
| 2007/0043353 A1 | 2/2007 | Dycus et al. | 2009/0275865 A1 | 11/2009 | Zhao et al. |
| 2007/0062017 A1 | 3/2007 | Dycus et al. | 2009/0292282 A9 | 11/2009 | Dycus |
| 2007/0118115 A1 | 5/2007 | Artale et al. | 2009/0299364 A1 | 12/2009 | Batchelor et al. |
| 2007/0173811 A1 | 7/2007 | Couture et al. | 2009/0312273 A1 | 12/2009 | De La Torre |
| 2007/0173813 A1 | 7/2007 | Odom | 2009/0318912 A1 | 12/2009 | Mayer et al. |
| 2007/0198011 A1 | 8/2007 | Sugita | 2010/0016857 A1 | 1/2010 | McKenna et al. |
| 2007/0225695 A1 | 9/2007 | Mayer et al. | 2010/0023009 A1 | 1/2010 | Moses et al. |
| 2007/0260238 A1 | 11/2007 | Guerra | 2010/0036375 A1 | 2/2010 | Regadas |
| 2007/0260242 A1 | 11/2007 | Dycus et al. | 2010/0042143 A1 | 2/2010 | Cunningham |
| 2007/0265616 A1 | 11/2007 | Couture et al. | 2010/0049187 A1 | 2/2010 | Carlton et al. |
| 2007/0265620 A1 | 11/2007 | Kraas et al. | 2010/0049194 A1 | 2/2010 | Hart et al. |
| 2008/0004616 A1 | 1/2008 | Patrick | 2010/0057078 A1 | 3/2010 | Arts et al. |
| 2008/0015563 A1 | 1/2008 | Hoey et al. | 2010/0057081 A1 | 3/2010 | Hanna |
| 2008/0015575 A1 | 1/2008 | Odom et al. | 2010/0057082 A1 | 3/2010 | Hanna |
| 2008/0033428 A1 | 2/2008 | Artale et al. | 2010/0057083 A1 | 3/2010 | Hanna |
| 2008/0046122 A1 | 2/2008 | Manzo et al. | 2010/0057084 A1 | 3/2010 | Hanna |
| 2008/0058802 A1 | 3/2008 | Couture et al. | 2010/0063500 A1 | 3/2010 | Muszala |
| 2008/0125797 A1 | 5/2008 | Kelleher | 2010/0069903 A1 | 3/2010 | Allen, IV et al. |
| 2008/0171938 A1 | 7/2008 | Masuda et al. | 2010/0069904 A1 | 3/2010 | Cunningham |
| 2008/0172051 A1 | 7/2008 | Masuda et al. | 2010/0069953 A1 | 3/2010 | Cunningham et al. |
| 2008/0215050 A1 | 9/2008 | Bakos | 2010/0076427 A1 | 3/2010 | Heard |
| 2008/0234672 A1 | 9/2008 | Bastian | 2010/0076430 A1 | 3/2010 | Romero |
| 2008/0234701 A1 | 9/2008 | Morales et al. | 2010/0076431 A1 | 3/2010 | Allen, IV |
| 2008/0243106 A1 | 10/2008 | Coe et al. | 2010/0076432 A1 | 3/2010 | Horner |
| 2008/0243120 A1 | 10/2008 | Lawes et al. | 2010/0087816 A1 | 4/2010 | Roy |
| 2008/0243158 A1 | 10/2008 | Morgan | 2010/0094271 A1 | 4/2010 | Ward et al. |
| 2008/0249523 A1 | 10/2008 | McPherson et al. | 2010/0094287 A1 | 4/2010 | Cunningham et al. |
| 2008/0249527 A1 | 10/2008 | Couture | 2010/0094289 A1 | 4/2010 | Taylor et al. |
| 2008/0271360 A1 | 11/2008 | Barfield | 2010/0100122 A1 | 4/2010 | Hinton |
| 2008/0281311 A1 | 11/2008 | Dunning et al. | 2010/0130971 A1 | 5/2010 | Baily |
| 2008/0319292 A1 | 12/2008 | Say et al. | 2010/0130977 A1 | 5/2010 | Garrison et al. |
| 2009/0012520 A1 | 1/2009 | Hixson et al. | 2010/0168741 A1 | 7/2010 | Sanai et al. |
| 2009/0012556 A1 | 1/2009 | Boudreaux et al. | 2010/0179543 A1 | 7/2010 | Johnson et al. |
| 2009/0024126 A1 | 1/2009 | Artale et al. | 2010/0179545 A1 | 7/2010 | Twomey et al. |
| 2009/0036881 A1 | 2/2009 | Artale et al. | 2010/0179546 A1 | 7/2010 | Cunningham |
| 2009/0036899 A1 | 2/2009 | Carlton et al. | 2010/0179547 A1 | 7/2010 | Cunningham et al. |
| 2009/0043304 A1 | 2/2009 | Tetzlaff et al. | 2010/0198218 A1 | 8/2010 | Manzo |
| 2009/0048596 A1 | 2/2009 | Shields et al. | 2010/0198248 A1 | 8/2010 | Vakharia |
| 2009/0054894 A1 | 2/2009 | Yachi | 2010/0204697 A1 | 8/2010 | Dumbauld et al. |
| 2009/0062794 A1 | 3/2009 | Buysse et al. | 2010/0204698 A1 | 8/2010 | Chapman et al. |
| 2009/0065565 A1 | 3/2009 | Cao | 2010/0217258 A1 | 8/2010 | Floume et al. |
| 2009/0076506 A1 | 3/2009 | Baker | 2010/0217264 A1 | 8/2010 | Odom et al. |
| 2009/0082766 A1 | 3/2009 | Unger et al. | 2010/0228249 A1 | 9/2010 | Mohr et al. |
| 2009/0088739 A1 | 4/2009 | Hushka et al. | 2010/0228250 A1 | 9/2010 | Brogna |

| | | | | | | |
|---|---|---|---|---|---|---|
| 2010/0249769 A1 | 9/2010 | Nau, Jr. et al. | | 2012/0059371 A1 | 3/2012 | Anderson et al. |
| 2010/0274160 A1 | 10/2010 | Yachi et al. | | 2012/0059372 A1 | 3/2012 | Johnson |
| 2010/0274244 A1 | 10/2010 | Heard | | 2012/0059374 A1 | 3/2012 | Johnson et al. |
| 2010/0274265 A1 | 10/2010 | Wingardner et al. | | 2012/0059375 A1 | 3/2012 | Couture et al. |
| 2010/0280511 A1 | 11/2010 | Rachlin et al. | | 2012/0059408 A1 | 3/2012 | Mueller |
| 2010/0292691 A1 | 11/2010 | Brogna | | 2012/0059409 A1 | 3/2012 | Reschke et al. |
| 2010/0305558 A1 | 12/2010 | Kimura et al. | | 2012/0078250 A1 | 3/2012 | Orton et al. |
| 2010/0307934 A1 | 12/2010 | Chowaniec et al. | | 2012/0083785 A1 | 4/2012 | Roy et al. |
| 2010/0312235 A1 | 12/2010 | Bahney | | 2012/0083786 A1 | 4/2012 | Artale et al. |
| 2010/0331742 A1 | 12/2010 | Masuda | | 2012/0083827 A1 | 4/2012 | Artale et al. |
| 2010/0331839 A1 | 12/2010 | Schechter et al. | | 2012/0095456 A1 | 4/2012 | Schechter et al. |
| 2011/0004210 A1 | 1/2011 | Johnson et al. | | 2012/0095460 A1 | 4/2012 | Rooks et al. |
| 2011/0015632 A1 | 1/2011 | Artale | | 2012/0109187 A1 | 5/2012 | Gerhardt, Jr. et al. |
| 2011/0018164 A1 | 1/2011 | Sartor et al. | | 2012/0118507 A1 | 5/2012 | Brandt et al. |
| 2011/0034918 A1 | 2/2011 | Reschke | | 2012/0123402 A1 | 5/2012 | Chernov et al. |
| 2011/0046623 A1 | 2/2011 | Reschke | | 2012/0123404 A1 | 5/2012 | Craig |
| 2011/0054467 A1 | 3/2011 | Mueller et al. | | 2012/0123410 A1 | 5/2012 | Craig |
| 2011/0054468 A1 | 3/2011 | Dycus | | 2012/0123413 A1 | 5/2012 | Chernov et al. |
| 2011/0054469 A1 | 3/2011 | Kappus et al. | | 2012/0130367 A1 | 5/2012 | Garrison |
| 2011/0054471 A1 | 3/2011 | Gerhardt et al. | | 2012/0136353 A1 | 5/2012 | Romero |
| 2011/0054472 A1 | 3/2011 | Romero | | 2012/0136354 A1 | 5/2012 | Rupp |
| 2011/0060333 A1 | 3/2011 | Mueller | | 2012/0143185 A1 | 6/2012 | Nau, Jr. |
| 2011/0060334 A1 | 3/2011 | Brandt et al. | | 2012/0165797 A1 | 6/2012 | Cunningham |
| 2011/0060335 A1 | 3/2011 | Harper et al. | | 2012/0165818 A1 | 6/2012 | Odom |
| 2011/0071523 A1 | 3/2011 | Dickhans | | 2012/0172868 A1 | 7/2012 | Twomey et al. |
| 2011/0071525 A1 | 3/2011 | Dumbauld et al. | | 2012/0172873 A1 | 7/2012 | Artale et al. |
| 2011/0072638 A1 | 3/2011 | Brandt et al. | | 2012/0172924 A1 | 7/2012 | Allen, IV |
| 2011/0073594 A1 | 3/2011 | Bonn | | 2012/0172925 A1 | 7/2012 | Dumbauld et al. |
| 2011/0077637 A1 | 3/2011 | Brannan | | 2012/0184989 A1 | 7/2012 | Twomey |
| 2011/0077648 A1 | 3/2011 | Lee et al. | | 2012/0184990 A1 | 7/2012 | Twomey |
| 2011/0077649 A1 | 3/2011 | Kingsley | | 2012/0202179 A1 | 8/2012 | Fedotov et al. |
| 2011/0082457 A1 | 4/2011 | Kerr et al. | | 2012/0209263 A1 | 8/2012 | Sharp et al. |
| 2011/0082494 A1 | 4/2011 | Kerr et al. | | 2012/0215219 A1 | 8/2012 | Roy et al. |
| 2011/0087221 A1 | 4/2011 | Siebrecht et al. | | 2012/0215242 A1 | 8/2012 | Reschke et al. |
| 2011/0098689 A1 | 4/2011 | Nau, Jr. et al. | | | | |
| 2011/0106079 A1 | 5/2011 | Garrison et al. | | FOREIGN PATENT DOCUMENTS | | |
| 2011/0118736 A1 | 5/2011 | Harper et al. | | | | |
| 2011/0178519 A1 | 7/2011 | Couture et al. | | CA | 2590520 A1 | 11/2007 |
| 2011/0184405 A1 | 7/2011 | Mueller | | CN | 201299462 | 9/2009 |
| 2011/0190653 A1 | 8/2011 | Harper et al. | | DE | 2415263 A1 | 10/1975 |
| 2011/0190765 A1 | 8/2011 | Chojin | | DE | 02514501 A1 | 10/1976 |
| 2011/0193608 A1 | 8/2011 | Krapohl | | DE | 2627679 A1 | 1/1977 |
| 2011/0218530 A1 | 9/2011 | Reschke | | DE | 03423356 C2 | 6/1986 |
| 2011/0230880 A1 | 9/2011 | Chojin et al. | | DE | 03612646 A1 | 4/1987 |
| 2011/0238066 A1 | 9/2011 | Olson | | DE | 8712328 U1 | 2/1988 |
| 2011/0238067 A1 | 9/2011 | Moses et al. | | DE | 04303882 C2 | 2/1995 |
| 2011/0251605 A1 | 10/2011 | Hoarau et al. | | DE | 04403252 A1 | 8/1995 |
| 2011/0251606 A1 | 10/2011 | Kerr | | DE | 19515914 C1 | 7/1996 |
| 2011/0251611 A1 | 10/2011 | Horner et al. | | DE | 19506363 A1 | 8/1996 |
| 2011/0257680 A1 | 10/2011 | Reschke et al. | | DE | 29616210 U1 | 11/1996 |
| 2011/0257681 A1 | 10/2011 | Reschke et al. | | DE | 19608716 C1 | 4/1997 |
| 2011/0270245 A1 | 11/2011 | Horner et al. | | DE | 19751106 A1 | 5/1998 |
| 2011/0270250 A1 | 11/2011 | Horner et al. | | DE | 19751108 A1 | 5/1999 |
| 2011/0270251 A1 | 11/2011 | Horner et al. | | DE | 19946527 C1 | 7/2001 |
| 2011/0270252 A1 | 11/2011 | Horner et al. | | DE | 20121161 U1 | 4/2002 |
| 2011/0276048 A1 | 11/2011 | Kerr et al. | | DE | 10045375 C2 | 10/2002 |
| 2011/0276049 A1 | 11/2011 | Gerhardt | | DE | 202007009165 U1 | 8/2007 |
| 2011/0295251 A1 | 12/2011 | Garrison | | DE | 202007009317 U1 | 8/2007 |
| 2011/0295313 A1 | 12/2011 | Kerr | | DE | 202007009318 U1 | 8/2007 |
| 2011/0301592 A1 | 12/2011 | Kerr et al. | | DE | 10031773 B4 | 11/2007 |
| 2011/0301599 A1 | 12/2011 | Roy et al. | | DE | 202007016233 U1 | 1/2008 |
| 2011/0301600 A1 | 12/2011 | Garrison et al. | | DE | 19738457 B4 | 1/2009 |
| 2011/0301601 A1 | 12/2011 | Garrison et al. | | DE | 102004026179 B4 | 1/2009 |
| 2011/0301602 A1 | 12/2011 | Roy et al. | | DE | 102008018406 B3 | 7/2009 |
| 2011/0301603 A1 | 12/2011 | Kerr et al. | | EP | 0467501 A1 | 1/1992 |
| 2011/0301604 A1 | 12/2011 | Horner et al. | | EP | 0509670 A3 | 12/1992 |
| 2011/0301605 A1 | 12/2011 | Horner | | EP | 0306123 B1 | 8/1993 |
| 2011/0301606 A1 | 12/2011 | Kerr | | EP | 0572131 A1 | 12/1993 |
| 2011/0301637 A1 | 12/2011 | Kerr et al. | | EP | 0584787 A1 | 3/1994 |
| 2011/0319886 A1 | 12/2011 | Chojin et al. | | EP | 0589555 A1 | 3/1994 |
| 2011/0319888 A1 | 12/2011 | Mueller et al. | | EP | 0589453 A3 | 4/1994 |
| 2012/0004658 A1 | 1/2012 | Chojin | | EP | 0648475 A1 | 4/1995 |
| 2012/0010614 A1 | 1/2012 | Couture | | EP | 0624348 A3 | 6/1995 |
| 2012/0022532 A1 | 1/2012 | Garrison | | EP | 0364216 B1 | 1/1996 |
| 2012/0029515 A1 | 2/2012 | Couture | | EP | 0518230 B1 | 5/1996 |
| 2012/0041438 A1 | 2/2012 | Nau, Jr. et al. | | EP | 0517243 B1 | 9/1997 |
| 2012/0046659 A1 | 2/2012 | Mueller | | EP | 0541930 B1 | 3/1998 |
| 2012/0046660 A1 | 2/2012 | Nau, Jr. | | EP | 0878169 A1 | 11/1998 |
| 2012/0046662 A1 | 2/2012 | Gilbert | | EP | 0623316 B1 | 3/1999 |
| | | | | EP | 0650701 B1 | 3/1999 |

| | | | | | | |
|---|---|---|---|---|---|---|
| EP | 0923907 A1 | 6/1999 | | GB | 623316 | 5/1949 |
| EP | 0640317 B1 | 9/1999 | | GB | 1490585 | 11/1977 |
| EP | 0950378 A1 | 10/1999 | | GB | 2213416 A | 8/1989 |
| EP | 0986990 A1 | 3/2000 | | GB | 2214430 A | 9/1989 |
| EP | 1034747 A1 | 9/2000 | | JP | 61-501068 | 9/1984 |
| EP | 1034748 | 9/2000 | | JP | 10-24051 A | 1/1989 |
| EP | 0694290 B1 | 11/2000 | | JP | 11-47150 A | 6/1989 |
| EP | 1050278 | 11/2000 | | JP | 6-502328 | 3/1992 |
| EP | 1053719 | 11/2000 | | JP | 5-5106 | 1/1993 |
| EP | 1053720 | 11/2000 | | JP | 05-40112 | 2/1993 |
| EP | 1055399 | 11/2000 | | JP | 0006030945 A | 2/1994 |
| EP | 1055400 | 11/2000 | | JP | 6-121797 A | 5/1994 |
| EP | 1080694 | 3/2001 | | JP | 6-285078 A | 10/1994 |
| EP | 1082944 | 3/2001 | | JP | 6-511401 | 12/1994 |
| EP | 1 159 926 A2 | 12/2001 | | JP | 06343644 A | 12/1994 |
| EP | 1177771 | 2/2002 | | JP | 07265328 A | 10/1995 |
| EP | 1278007 | 1/2003 | | JP | 8-56955 | 5/1996 |
| EP | 0717966 B1 | 4/2003 | | JP | 08252263 A | 10/1996 |
| EP | 1301135 | 4/2003 | | JP | 8-289895 A | 11/1996 |
| EP | 0887046 B1 | 7/2003 | | JP | 8-317934 A | 12/1996 |
| EP | 1330991 | 7/2003 | | JP | 8-317936 A | 12/1996 |
| EP | 1486177 | 6/2004 | | JP | 9-10223 C | 1/1997 |
| EP | 0913126 B1 | 10/2004 | | JP | 9-122138 A | 5/1997 |
| EP | 1472984 | 11/2004 | | JP | 0010000195 A | 1/1998 |
| EP | 0754437 B2 | 12/2004 | | JP | 10-155798 A | 6/1998 |
| EP | 0888747 B1 | 12/2004 | | JP | 11-070124 A | 3/1999 |
| EP | 1025807 B1 | 12/2004 | | JP | 11-169381 A | 6/1999 |
| EP | 0774232 B1 | 1/2005 | | JP | 11-192238 A | 7/1999 |
| EP | 0853922 B1 | 2/2005 | | JP | 11244298 A | 9/1999 |
| EP | 1527747 | 5/2005 | | JP | 2000-102545 A | 4/2000 |
| EP | 1530952 | 5/2005 | | JP | 2000342599 A | 12/2000 |
| EP | 1532932 | 5/2005 | | JP | 2000350732 A | 12/2000 |
| EP | 1535581 | 6/2005 | | JP | 2001008944 A | 1/2001 |
| EP | 1609430 | 12/2005 | | JP | 2001029356 A | 2/2001 |
| EP | 1201192 | 2/2006 | | JP | 2001-03400 | 4/2001 |
| EP | 1034746 B1 | 3/2006 | | JP | 2001128990 A | 5/2001 |
| EP | 1632192 | 3/2006 | | JP | 2001-190564 A | 7/2001 |
| EP | 1186274 | 4/2006 | | JP | 2002-136525 A | 5/2002 |
| EP | 1642543 | 4/2006 | | JP | 2002-528166 A | 9/2002 |
| EP | 1645238 | 4/2006 | | JP | 2003-175052 A | 6/2003 |
| EP | 1645240 | 4/2006 | | JP | 2003245285 A | 9/2003 |
| EP | 1649821 | 4/2006 | | JP | 2004-517668 A | 6/2004 |
| EP | 0875209 B1 | 5/2006 | | JP | 2004-528869 A | 9/2004 |
| EP | 1685806 | 8/2006 | | JP | 2005-253789 A | 9/2005 |
| EP | 1707143 | 10/2006 | | JP | 2006-015078 A | 1/2006 |
| EP | 1545360 | 3/2007 | | JP | 2006-501939 A | 1/2006 |
| EP | 1767163 | 3/2007 | | JP | 2006-095316 A | 4/2006 |
| EP | 1767164 | 3/2007 | | JP | 2011125195 A | 6/2011 |
| EP | 1769765 | 4/2007 | | SU | 401367 A1 | 10/1973 |
| EP | 1769766 | 4/2007 | | WO | 89/00757 | 1/1989 |
| EP | 1772109 | 4/2007 | | WO | 92/04873 | 4/1992 |
| EP | 1785097 | 5/2007 | | WO | 92/06642 | 4/1992 |
| EP | 1785098 | 5/2007 | | WO | 93/19681 | 10/1993 |
| EP | 1785101 | 5/2007 | | WO | 93/21845 | 11/1993 |
| EP | 1787597 | 5/2007 | | WO | 94/00059 | 1/1994 |
| EP | 1810625 | 7/2007 | | WO | 94/08524 | 4/1994 |
| EP | 1810628 | 7/2007 | | WO | 94/20025 | 9/1994 |
| EP | 1842500 | 10/2007 | | WO | 95/02369 | 1/1995 |
| EP | 1878400 | 1/2008 | | WO | 95/07662 | 3/1995 |
| EP | 1894535 | 3/2008 | | WO | 95/15124 | 6/1995 |
| EP | 1929970 | 6/2008 | | WO | 95/20360 | 8/1995 |
| EP | 1946715 | 7/2008 | | WO | 95/20921 | 8/1995 |
| EP | 1958583 | 8/2008 | | WO | 96/05776 | 2/1996 |
| EP | 1990019 | 11/2008 | | WO | 96/11635 | 4/1996 |
| EP | 1994904 | 11/2008 | | WO | 96/22056 | 7/1996 |
| EP | 1683496 | 12/2008 | | WO | 96/13218 | 9/1996 |
| EP | 1997438 | 12/2008 | | WO | 97/00646 | 1/1997 |
| EP | 1997439 | 12/2008 | | WO | 97/00647 | 1/1997 |
| EP | 1527744 | 2/2009 | | WO | 97/10764 | 3/1997 |
| EP | 2103268 | 9/2009 | | WO | 97/18768 | 5/1997 |
| EP | 2105104 | 9/2009 | | WO | 97/24073 | 7/1997 |
| EP | 2147649 | 1/2010 | | WO | 97/24993 | 7/1997 |
| EP | 2153791 | 2/2010 | | WO | 98/14124 | 4/1998 |
| EP | 2206474 | 7/2010 | | WO | 98/27880 | 7/1998 |
| EP | 1920725 | 10/2010 | | WO | 98/31290 | 7/1998 |
| EP | 2243439 | 10/2010 | | WO | 98/43264 | 10/1998 |
| EP | 2294998 | 3/2011 | | WO | 99/03407 | 1/1999 |
| EP | 2301467 | 3/2011 | | WO | 99/03408 | 1/1999 |
| EP | 1628586 | 7/2011 | | WO | 99/03409 | 1/1999 |

| | | |
|---|---|---|
| WO | 99/03414 | 1/1999 |
| WO | 99/12488 | 3/1999 |
| WO | 99/23933 | 5/1999 |
| WO | 99/23959 | 5/1999 |
| WO | 99/25261 | 5/1999 |
| WO | 99/40857 | 8/1999 |
| WO | 99/40861 | 8/1999 |
| WO | 99/51158 | 10/1999 |
| WO | 99/66850 | 12/1999 |
| WO | 00/24322 | 5/2000 |
| WO | 00/24330 | 5/2000 |
| WO | 00/24331 | 5/2000 |
| WO | 00/33753 | 6/2000 |
| WO | 0036986 A1 | 6/2000 |
| WO | 00/41638 | 7/2000 |
| WO | 00/47124 | 8/2000 |
| WO | 00/53112 | 9/2000 |
| WO | 0059392 A1 | 10/2000 |
| WO | 01/01847 | 1/2001 |
| WO | 0100114 A1 | 1/2001 |
| WO | 01/17448 | 3/2001 |
| WO | 0115614 A1 | 3/2001 |
| WO | 0154604 A1 | 8/2001 |
| WO | 01/66025 | 9/2001 |
| WO | 02/07627 | 1/2002 |
| WO | 02/058544 | 8/2002 |
| WO | 02/067798 | 9/2002 |
| WO | 02045589 A3 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080793 | 10/2002 |
| WO | 02/080794 | 10/2002 |
| WO | 02/080795 | 10/2002 |
| WO | 02/080796 | 10/2002 |
| WO | 02/080797 | 10/2002 |
| WO | 02/080798 | 10/2002 |
| WO | 02/080799 | 10/2002 |
| WO | 02/081170 | 10/2002 |
| WO | 02/085218 | 10/2002 |
| WO | 02/094746 | 11/2002 |
| WO | 03/061500 | 7/2003 |
| WO | 03/068046 | 8/2003 |
| WO | 03/096880 | 11/2003 |
| WO | 03/101311 | 12/2003 |
| WO | 03/090630 A3 | 4/2004 |
| WO | 2004/028585 | 4/2004 |
| WO | 2004/032776 | 4/2004 |
| WO | 2004/032777 | 4/2004 |
| WO | 2004/052221 | 6/2004 |
| WO | 2004/073488 | 9/2004 |
| WO | 2004/073490 | 9/2004 |
| WO | 2004/073753 | 9/2004 |
| WO | 2004/082495 | 9/2004 |
| WO | 2004/083797 | 9/2004 |
| WO | 2004/098383 | 11/2004 |
| WO | 2004/103156 | 12/2004 |
| WO | 2005/004734 | 1/2005 |
| WO | 2005/004735 | 1/2005 |
| WO | 2005/009255 | 2/2005 |
| WO | 2005/011049 | 2/2005 |
| WO | 2005/030071 | 4/2005 |
| WO | 2005/048809 | 6/2005 |
| WO | 2005/050151 | 6/2005 |
| WO | 2006/021269 A1 | 3/2006 |
| WO | 2005110264 A3 | 4/2006 |
| WO | 2008/008457 | 1/2008 |
| WO | 2008/040483 A1 | 4/2008 |
| WO | 2008/045348 | 4/2008 |
| WO | 2008/045350 | 4/2008 |
| WO | 2008/112147 | 9/2008 |
| WO | 2009/005850 | 1/2009 |
| WO | 2009/032623 | 3/2009 |
| WO | 2009/039179 | 3/2009 |
| WO | 2009/039510 | 3/2009 |
| WO | 2009/124097 | 10/2009 |
| WO | 2010/104753 | 9/2010 |

OTHER PUBLICATIONS

U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
U.S. Appl. No. 13/050,182, Glenn A. Horner.
U.S. Appl. No. 13/072,945, Patrick L. Dumbauld.
U.S. Appl. No. 13/080,383, David M. Garrison.
U.S. Appl. No. 13/085,144, Keir Hart.
U.S. Appl. No. 13/091,331, Jeffrey R. Townsend.
U.S. Appl. No. 13/102,573, John R. Twomey.
U.S. Appl. No. 13/102,604, Paul E. Ourada.
U.S. Appl. No. 13/108,093, Boris Chernov.
U.S. Appl. No. 13/108,129, Boris Chernov.
U.S. Appl. No. 13/108,152, Boris Chernov.
U.S. Appl. No. 13/108,177, Boris Chernov.
U.S. Appl. No. 13/108,196, Boris Chernov.
U.S. Appl. No. 13/108,441, Boris Chernov.
U.S. Appl. No. 13/108,468, Boris Chernov.
U.S. Appl. No. 13/111,642, John R. Twomey.
U.S. Appl. No. 13/111,678, Nikolay Kharin.
U.S. Appl. No. 13/113,231, David M. Garrison.
U.S. Appl. No. 13/157,047, John R. Twomey.
U.S. Appl. No. 13/162,814, Barbara R. Tyrrell.
U.S. Appl. No. 13/166,477, Daniel A. Joseph.
U.S. Appl. No. 13/166,497, Daniel A. Joseph.
U.S. Appl. No. 13/179,919, Russell D. Hempstead.
U.S. Appl. No. 13/179,960, Boris Chernov.
U.S. Appl. No. 13/179,975, Grant T. Sims.
U.S. Appl. No. 13/180,018, Chase Collings.
U.S. Appl. No. 13/183,856, John R. Twomey.
U.S. Appl. No. 13/185,593, James D. Allen, IV.
U.S. Appl. No. 13/204,841, Edward J. Chojin.
U.S. Appl. No. 13/205,999, Jeffrey R. Unger.
U.S. Appl. No. 13/212,297, Allan J. Evans.
U.S. Appl. No. 13/212,308, Allan J. Evans.
U.S. Appl. No. 13/212,329, Allan J. Evans.
U.S. Appl. No. 13/212,343, Duane E. Kerr.
U.S. Appl. No. 13/223,521, John R. Twomey.
U.S. Appl. No. 13/227,220, James D. Allen, IV.
U.S. Appl. No. 13/228,742, Duane E. Kerr.
U.S. Appl. No. 13/231,643, Keir Hart.
U.S. Appl. No. 13/234,357, James D. Allen, IV.
U.S. Appl. No. 13/236,168, James D. Allen, IV.
U.S. Appl. No. 13/236,271, Monte S. Fry.
U.S. Appl. No. 13/243,628, William Ross Whitney.
U.S. Appl. No. 13/247,778, John R. Twomey.
U.S. Appl. No. 13/247,795, John R. Twomey.
U.S. Appl. No. 13/248,976, James D. Allen, IV.
U.S. Appl. No. 13/249,013, Jeffrey R. Unger.
U.S. Appl. No. 13/249,024, John R. Twomey.
U.S. Appl. No. 13/251,380, Duane E. Kerr.
U.S. Appl. No. 13/277,373, Glenn A. Horner.
U.S. Appl. No. 13/277,926, David M. Garrison.
U.S. Appl. No. 13/277,962, David M. Garrison.
U.S. Appl. No. 13/293,754, Jeffrey M. Roy.
U.S. Appl. No. 13/306,523, David M. Garrison.
U.S. Appl. No. 13/306,553, Duane E. Kerr.
U.S. Appl. No. 13/308,104, John R. Twomey.
U.S. Appl. No. 13/312,172, Robert J. Behnke, II.
U.S. Appl. No. 13/324,863, William H. Nau, Jr.
U.S. Appl. No. 13/344,729, James D. Allen, IV.
U.S. Appl. No. 13/355,829, John R. Twomey.
U.S. Appl. No. 13/357,979, David M. Garrison.
U.S. Appl. No. 13/358,136, James D. Allen, IV.
U.S. Appl. No. 13/360,925, James H. Orszulak.
U.S. Appl. No. 13/400,290, Eric R. Larson.
U.S. Appl. No. 13/404,435, Kim V. Brandt.
U.S. Appl. No. 13/404,476, Kim V. Brandt.
U.S. Appl. No. 13/412,879, David M. Garrison.
U.S. Appl. No. 13/412,897, Joanna Ackley.
U.S. Appl. No. 13/421,373, John R. Twomey.

U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/464,569, Duane E. Kerr.
U.S. Appl. No. 13/466,274, Stephen M. Kendrick.
U.S. Appl. No. 13/467,767, Duane E. Kerr.
U.S. Appl. No. 13/470,543, Sean T. Dycus.
U.S. Appl. No. 13/470,775, James D. Allen, IV.
U.S. Appl. No. 13/470,797, John J. Kappus.
U.S. Appl. No. 13/482,589, Eric R. Larson.
U.S. Appl. No. 13/483,733, Dennis W. Butcher.
U.S. Appl. No. 13/488,093, Kristin D. Johnson.
U.S. Appl. No. 13/491,853, Jessica E. Olson.
U.S. Appl. No. 13/537,517, David N. Heard.
U.S. Appl. No. 13/537,577, Tony Moua.
U.S. Appl. No. 13/550,322, John J. Kappus.
U.S. Appl. No. 13/571,055, Paul Guerra.
U.S. Appl. No. 13/571,821, Joseph D. Bucciaglia.
U.S. Appl. No. 13/584,194, Sean T. Dycus.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71 9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

* cited by examiner

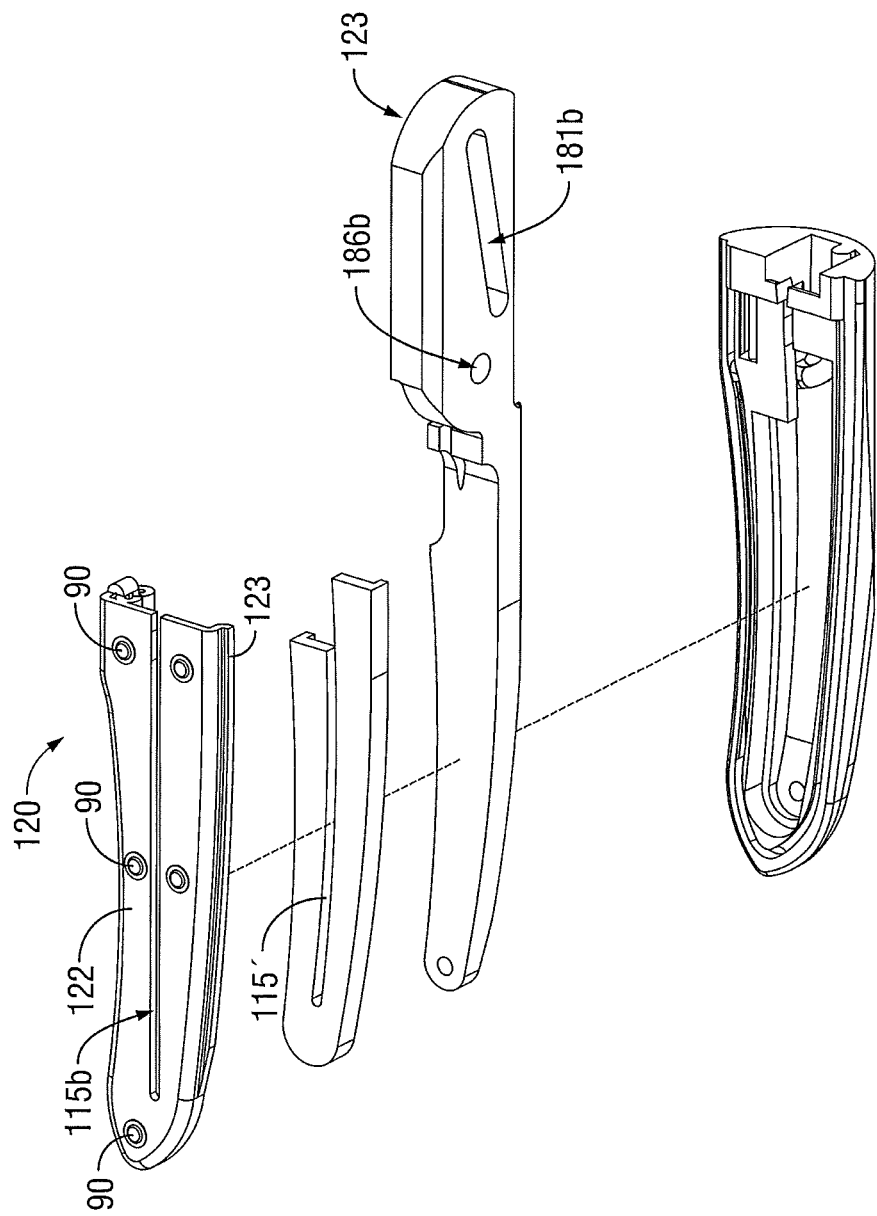

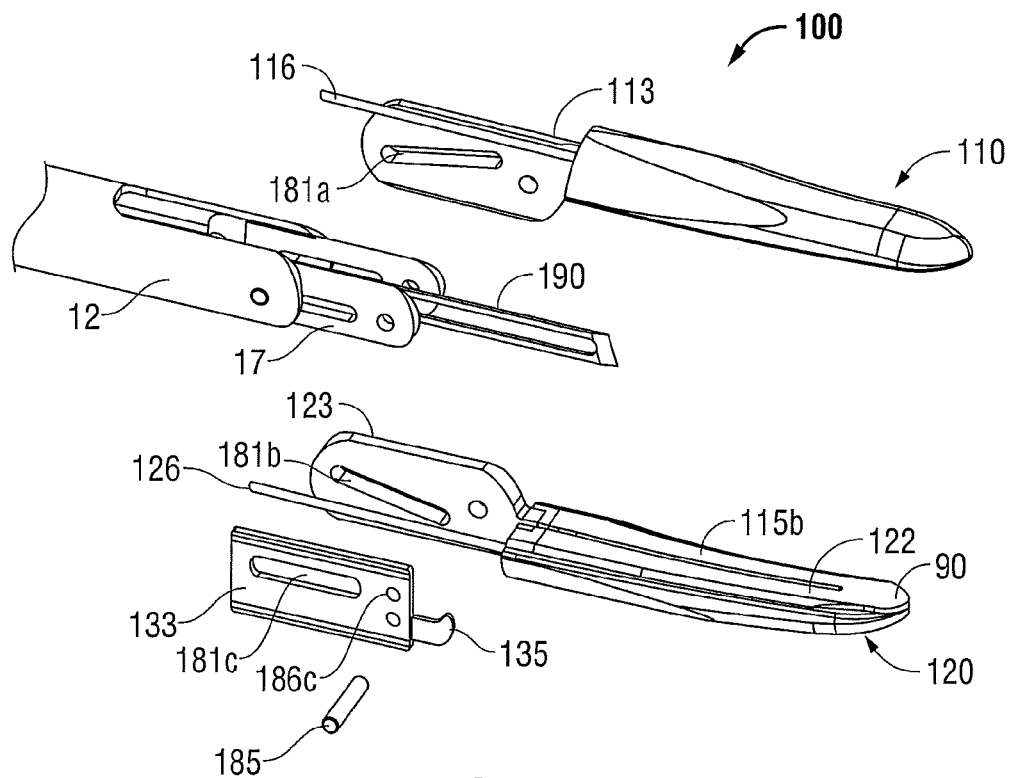
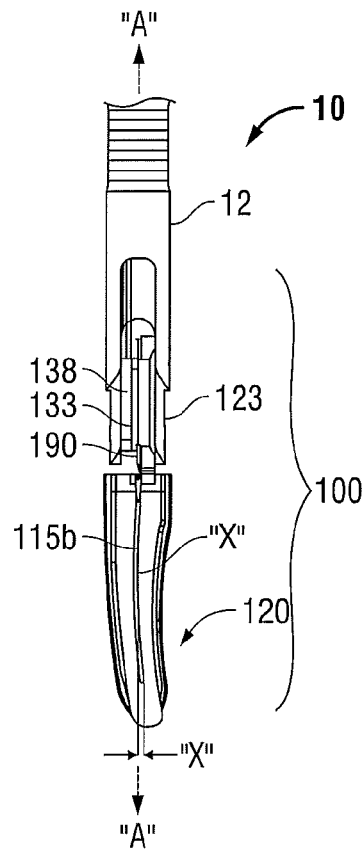

US 8,523,898 B2

ENDOSCOPIC ELECTROSURGICAL JAWS WITH OFFSET KNIFE

CROSS-REFERENCE TO RELATED APPLICATIONS

This application is a continuation of U.S. patent application No. 12/499,553, filed on Jul. 8, 2009, now U.S. Pat. No. 8,246,618, the entire contents of which are hereby incorporated by reference herein.

BACKGROUND

1. Technical Field

The present disclosure relates to an electrosurgical jaws and, more particularly, to an elongated endoscopic electrosurgical forceps with an offset knife for sealing and/or cutting tissue.

2. Background of Related Art

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

Typically, after a vessel or tissue is sealed, the surgeon advances a knife to sever the sealed tissue disposed between the opposing jaw members. In some instances, the knife blade is difficult to advance through the knife channel defined between jaw members or is subject to wear and tear over repeated use due to the relative position of the knife blade through the knife channel (contacting the sides of the knife channel).

SUMMARY

The present disclosure relates to an endoscopic forceps that includes a housing having a shaft attached thereto with a longitudinal axis defined therethrough. An end effector assembly is disposed at a distal end thereof and includes first and second jaw members disposed in opposing relation relative to one another and moveable from a first, open position to a second, closed position for grasping tissue therebetween. Each of the jaw members includes a proximal flange adapted to communicate with a drive assembly for moving the jaw members between the first and second positions. One or both of the of the jaw members has a curved knife channel (or a portion, e.g., distal portion, of the knife channel is curved) defined therein having a proximal end that is offset from the longitudinal axis defined through the shaft. A knife guide is assembled to an outer surface of one of the proximal flanges of the jaw members on the same side as the proximal end of the knife channel and defines a knife path therein configured to guide a knife into the knife channel for translation therethrough. One or more handles may be included that operably couple to the drive assembly for moving the jaw members between the first and second positions.

In one embodiment, the endoscopic forceps is an electrosurgical instrument and at least one of the jaw members is adapted to connect to an electrosurgical energy source to communicate energy to tissue disposed between the jaw members.

In another embodiment, the proximal flanges of the end effector and the knife guide include elongated slots defined therethrough that cooperate with a drive pin operably connected to the drive assembly to move the jaw members from the first to second positions. The elongated slots of the proximal flanges may be cam slots that operably engage the drive pin and the elongated slot of the knife guide may be a pass-through or non-engaging slot.

In yet another embodiment, the offset knife channel and the disposition of the knife guide relative to the longitudinal axis facilitate substantially straight extension of the knife through the knife channel along a substantial length of the knife channel. This configuration helps prevent binding of the knife during translation through the knife channel. The proximal end of the knife channel may be offset a distance "X" relative to the longitudinal axis "A" defined through the forceps, wherein "X" is in the range of about 0.010 inches to about 0.040 inches. The knife channel may be defined within both the first and second jaw members and the knife guide is configured to preload the jaw members during assembly for ensuring proper alignment of the knife channels to facilitate translation of the knife therethrough.

In still yet another embodiment, the knife guide includes one or more channels defined therein that are configured to guide a corresponding number of electrical leads to the jaw member(s) for supplying electrosurgical energy thereto.

The present disclosure also relates to an endoscopic forceps that includes a housing having a shaft attached thereto with a longitudinal axis defined therethrough and an end effector assembly disposed at a distal end thereof. The end effector assembly includes first and second jaw members disposed in opposing relation relative to one another and moveable from a first, open configuration to a second, closed configuration for grasping tissue therebetween. Each of the jaw members includes a proximal flange adapted to communicate with a drive assembly for moving the jaw members between the first and second positions. One or both of the of the jaw members has a knife channel defined therein having a proximal end that is offset from the longitudinal axis defined through the shaft. A knife guide is assembled to an outer surface of one of the proximal flanges of the jaw members on the same side as the proximal end of the knife channel and defines a knife path therein configured to guide a knife into the knife channel for translation therethrough. The knife guide includes a blade stop at a distal end thereof that is positionable from a first position that interferes with or obstructs the knife path to prevent distal translation of the knife when the jaw members are disposed in an first, open configuration to a second position that allows distal translation of the knife when the jaw members are disposed in the second, closed configuration. The blade stop may be pivotably engaged to the knife guide and biased to obstruct the knife path when the jaw members are disposed in the first, open configuration.

The forceps may include one or more handles that operably couple to a drive assembly for moving the jaw members between the first and second configurations. Moreover, the forceps may be an electrosurgical forceps wherein one or both of the jaw members are adapted to connect to an electrosurgical energy source to communicate energy to tissue disposed between the jaw members.

The proximal flanges of the end effector and the knife guide may include elongated slots defined therethrough that cooperate with a drive pin operably connected to the drive assembly to move the jaw members from the first to second configurations. The elongated slots of the proximal flanges may be cam slots that operably engage the drive pin and the elongated slot of the knife guide may be a pass-through or non-engaging slot.

In another embodiment, the offset knife channel and the disposition of the knife guide relative to the longitudinal axis may be configured to facilitate substantially straight extension of the knife through the knife channel along a substantial length of the knife channel. The proximal end of the knife channel may be offset a distance "X" relative to the longitudinal axis "A" defined through the forceps, wherein "X" is in the range of about 0.010 inches to about 0.040 inches.

In yet another embodiment, the knife guide includes one or more channels defined therein that are configured to guide a corresponding number of electrical leads to the jaw member for supplying electrosurgical energy thereto.

BRIEF DESCRIPTION OF THE DRAWINGS

Various embodiments of the subject instrument are described herein with reference to the drawings wherein:

FIG. 4A is a greatly-enlarged, perspective view of the bottom jaw of the end effector assembly with parts separated;

FIG. 6 is a partially exploded, perspective view of the end effector assembly;

FIG. 7 is a top view of the end effector assembly with the upper jaw member removed;

DETAILED DESCRIPTION

Figure 1A:
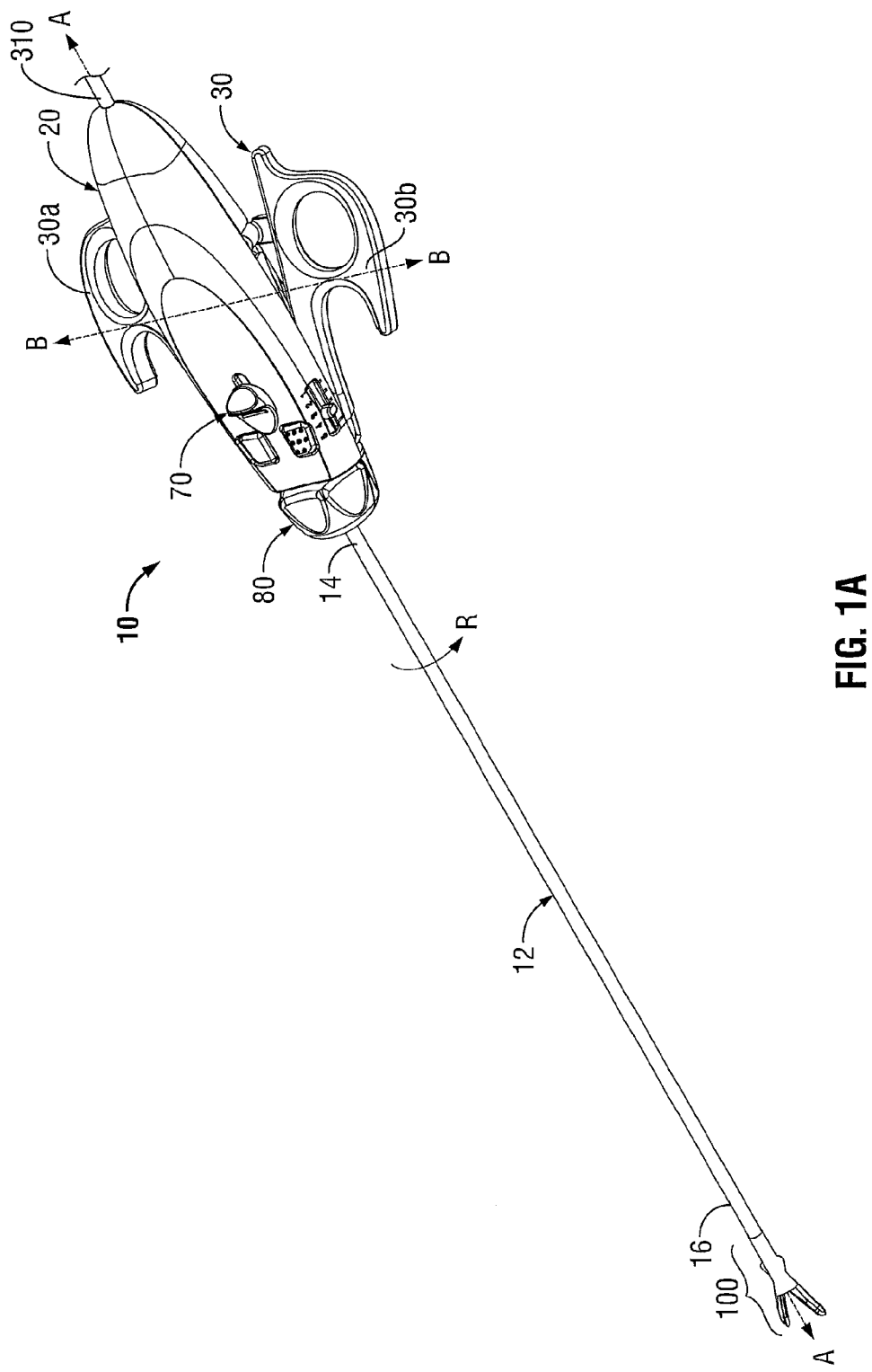
FIG. 1A is a top, perspective view of an endoscopic forceps shown in an open configuration and including a housing, a handle assembly, a shaft and an end effector assembly according to the present disclosure.
Figure 1B:
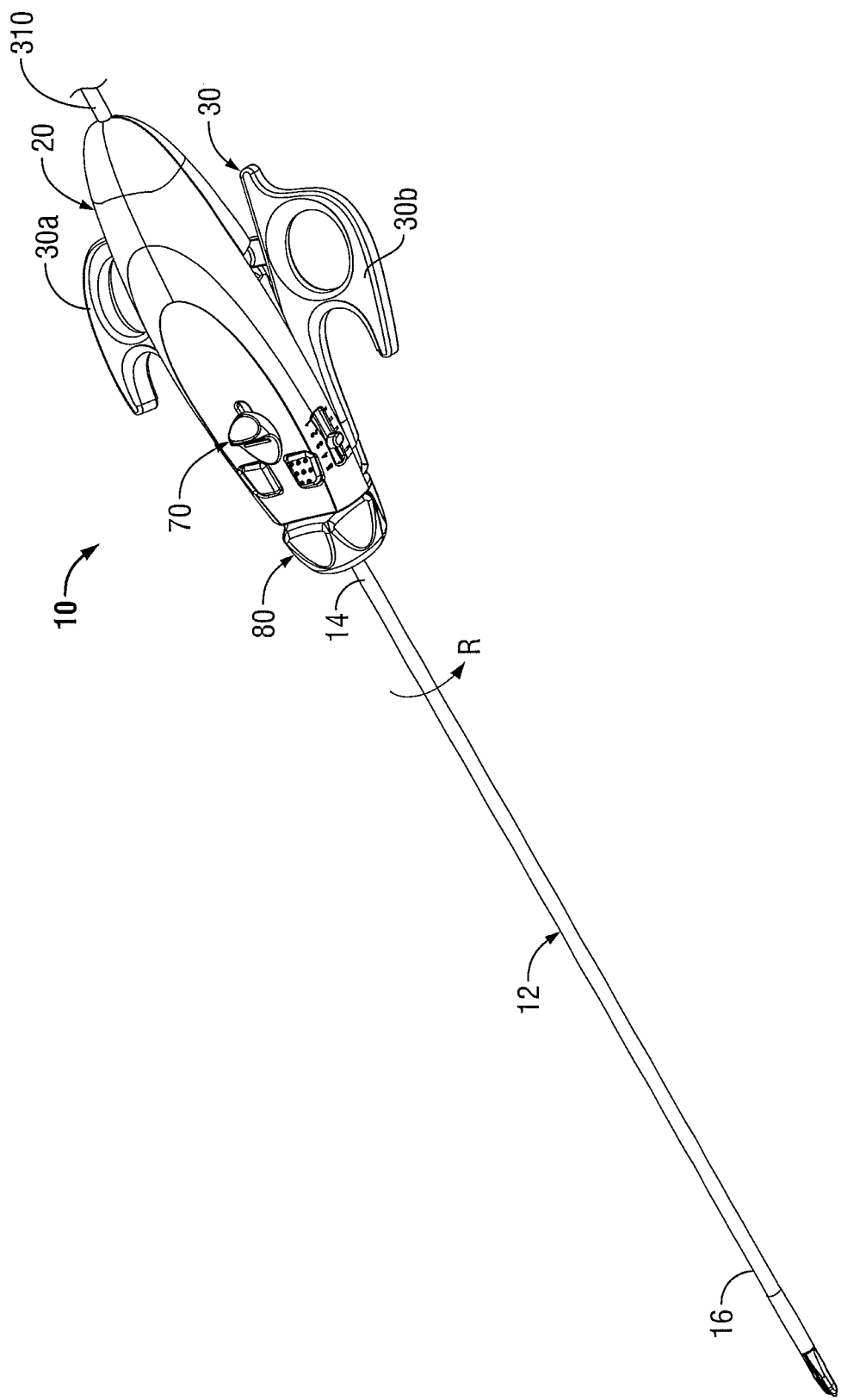
FIG. 1B is a top, perspective view of the endoscopic forceps of FIG. 1A showing the end effector assembly in a closed configuration according to the present disclosure.

Turning now to FIGS. 1A and 1B, one embodiment of an electrosurgical forceps 10 is shown for use with various surgical procedures and generally includes a housing 20, a handle assembly 30, a rotating assembly 80, a knife trigger assembly 70 and an end effector assembly 100 which mutually cooperate to grasp, seal and divide tubular vessels and vascular tissue. Although the majority of the figure drawings depict a forceps 10 for use in connection with endoscopic or laparoscopic surgical procedures, the present disclosure may be used for more traditional open surgical procedures. For the purposes herein, the forceps 10 is described in terms of an endoscopic or laparoscopic instrument; however, it is contemplated that an open version of the forceps may also include the same or similar operating components and features as described below.

Forceps 10 includes a shaft 12 that has a distal end 16 dimensioned to mechanically engage the end effector assembly 100 and a proximal end 14 that mechanically engages the housing 20. Details of how the shaft 12 connects to the end effector assembly 100 are described in more detail below. The proximal end 14 of shaft 12 is received within the housing 20 and the connections relating thereto are also described in detail below. In the drawings and in the descriptions that follow, the term "proximal", as is traditional, will refer to the end of the forceps 10 that is closer to the user, while the term "distal" will refer to the end that is further from the user.

Forceps 10 also includes an electrosurgical cable 310 that may connect the forceps 10 to a source of electrosurgical energy, e.g., a generator. Generators such as those sold by Covidien, located in Boulder, Colo. may be used as a source of both bipolar electrosurgical energy for sealing vessel and vascular tissues as well as monopolar electrosurgical energy which is typically employed to coagulate or cauterize tissue. It is envisioned that the generator may include various safety and performance features including isolated output, impedance control and/or independent activation of accessories.

Handle assembly 30 includes two movable handles 30a and 30b disposed on opposite sides of housing 20. Handles 30a and 30b are movable relative to one another to actuate the end effector assembly 100 as explained in more detail below with respect to the operation of the forceps 10.

Rotating assembly 80 is mechanically coupled to housing 20 and is rotatable approximately 90 degrees in either direction about a longitudinal axis "A." Rotating assembly 80, when rotated, rotates shaft 12, which, in turn, rotates end effector assembly 100. Such a configuration allows end effector assembly 100 to be rotated approximately 90 degrees in either direction with respect to housing 20.

As mentioned above, end effector assembly 100 is attached at the distal end 16 of shaft 12 and includes a pair of opposing jaw members 110 and 120 (see FIG. 6). Handles 30a and 30b of handle assembly 30 ultimately connect to drive assembly 60 (see FIG. 2A) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween.

Turning now to the more detailed features of the present disclosure as described with respect to FIGS. 1A-8C, handles 30a and 30b each include an aperture 33a and 33b, respectively, defined therein which enables a user to grasp and move each respective handle 30a and 30b relative to one another. Handles 30a and 30b also include ergonomically-enhanced gripping elements 39a and 39b, respectively, disposed along an outer edge thereof which are designed to facilitate gripping of the handles 30a and 30b during activation. It is envisioned that gripping elements 39a and 39b may include one or more protuberances, scallops and/or ribs to enhance gripping.

As best illustrated in FIG. 1A, handles 30a and 30b are configured to extend outwardly on opposite sides from a transverse axis "B" defined through housing 20 which is perpendicular to longitudinal axis "A". Handles 30a and 30b are movable relative to one another in a direction parallel to axis "B" to open and close the jaw members 110 and 120 as needed during surgery. Details relating to the inner-working components of forceps 10 are disclosed in commonly-owned U.S. patent application Ser. No. 11/540,335. This forceps style is commonly referred to as an "in-line" or hemostat style forceps. In-line hemostats or forceps are more commonly manufactured for open surgical procedures and typically include a pair of shafts having integrally coupled handles which are movable relative to one another to open and close the jaw members disposed at the distal end thereof.

Figure 2A:
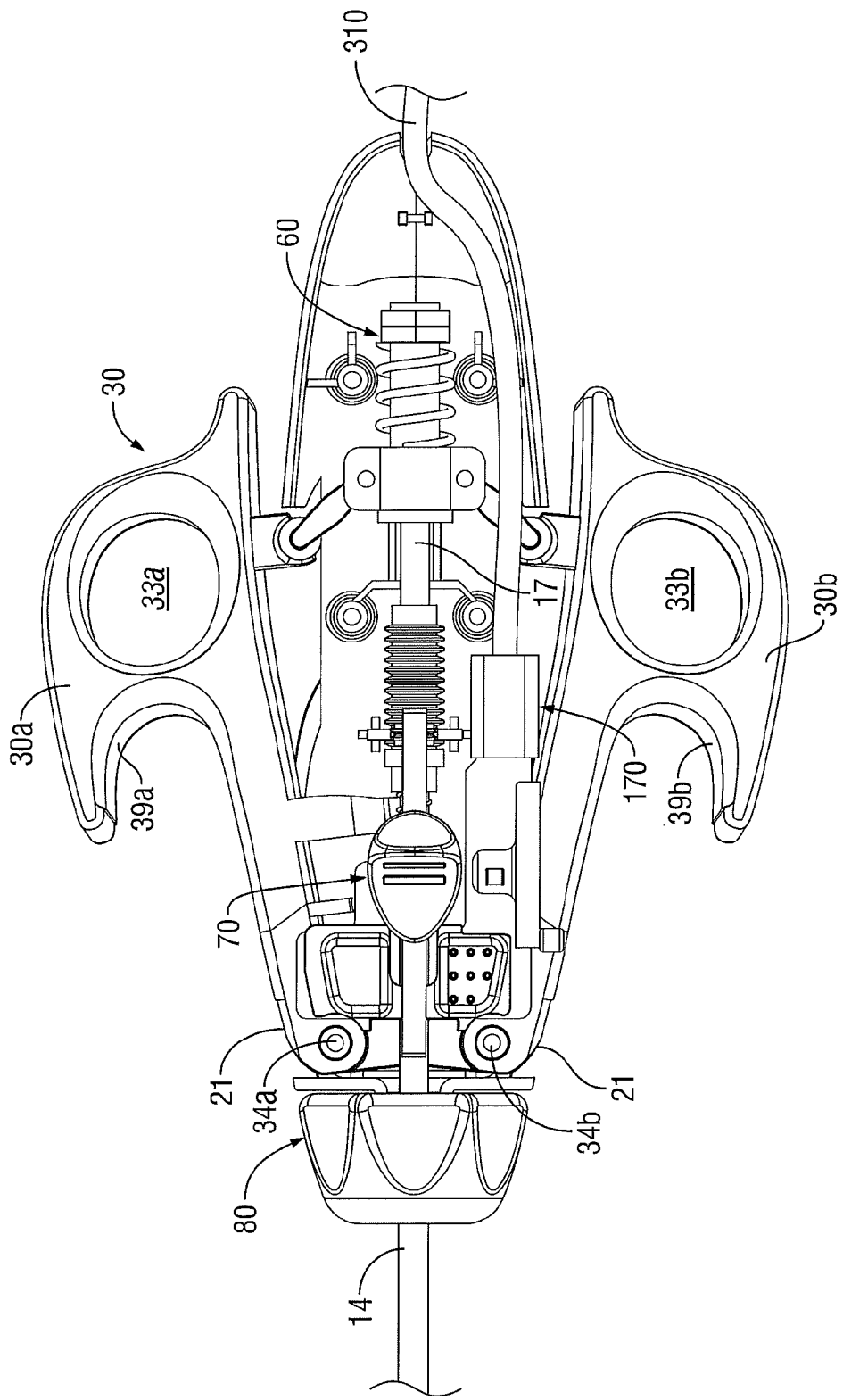
FIG. 2A is an enlarged, top view of the forceps of FIG. 1A showing the disposition of the internal components when the forceps is in an open configuration.
Figure 2B:
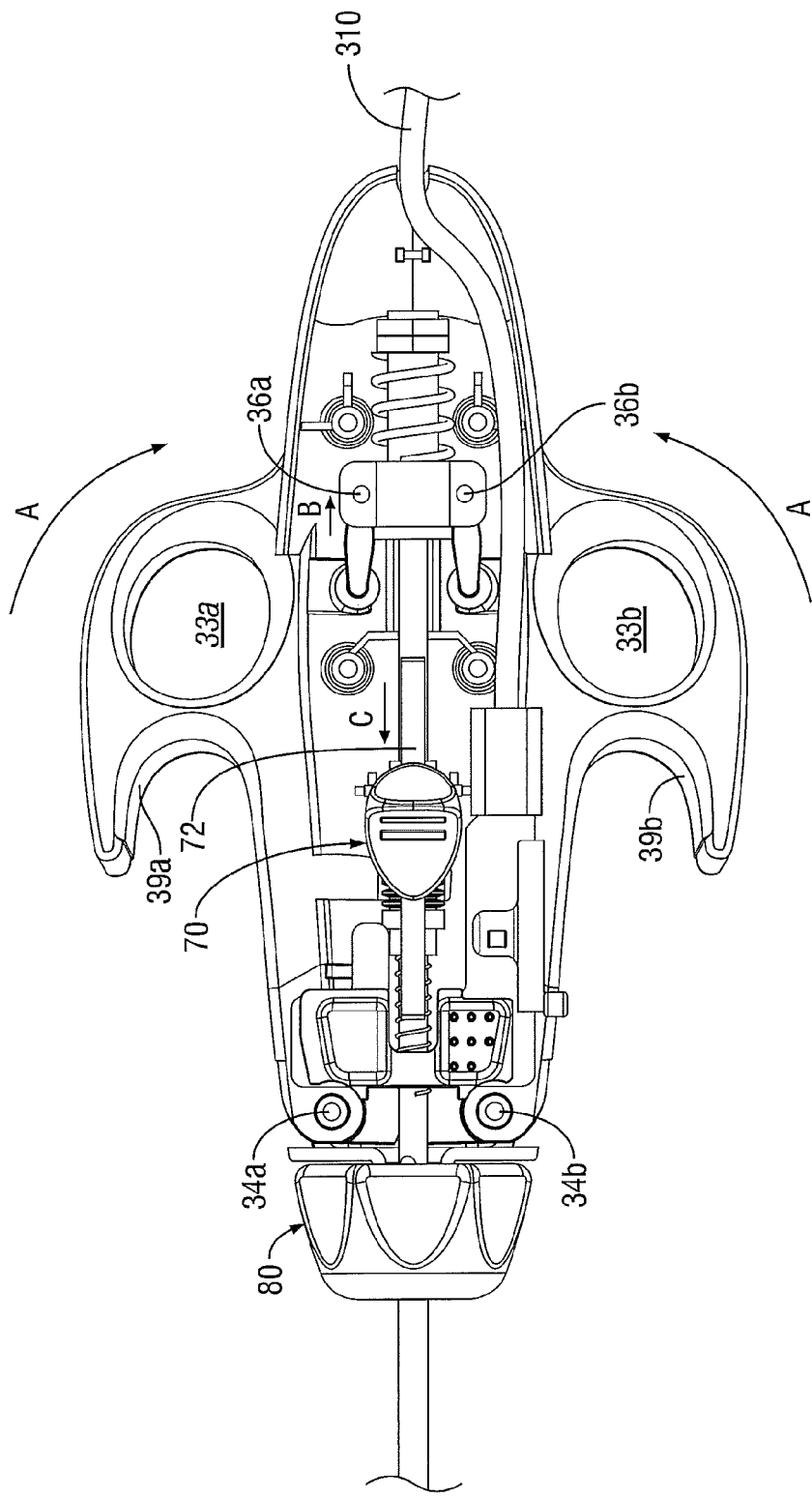
FIG. 2B is an enlarged, top view of the forceps of FIG. 1B showing the disposition of the internal components when the forceps is in a closed configuration.
Figure 3A:
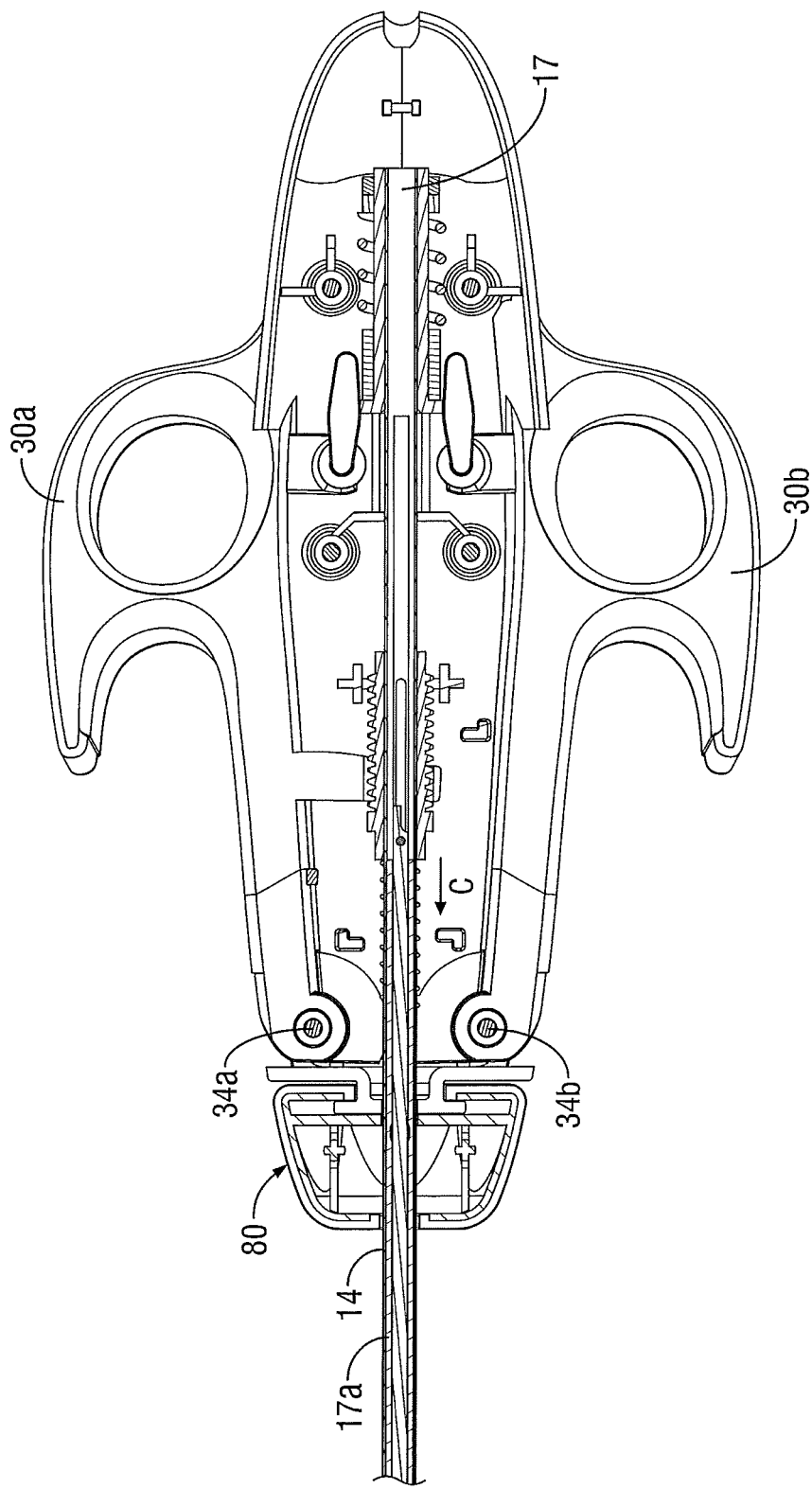
FIG. 3A is an enlarged, top view showing the knife actuator after actuation.
Figure 3B:
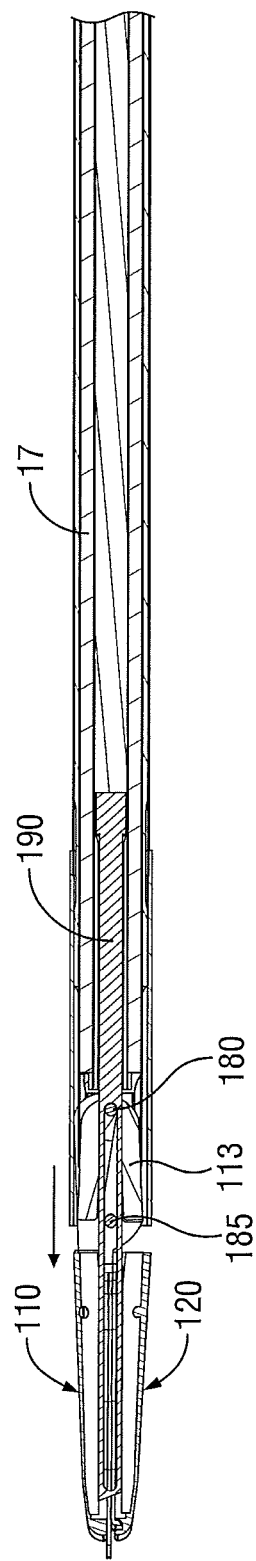
FIG. 3B is a greatly-enlarged, side cross sectional view of the end effector assembly showing the position of the knife after actuation.

As best seen in FIGS. 2A and 2B, the distal end of each handle 30a and 30b is selectively moveable about pivot pins 34a and 34b attached to a distal end 21 of the housing 20 to actuate the jaw members 110 and 120. Movement of the handles 30a and 30b away from one another (and the housing 20) unlocks and opens the handles 30a and 30b and, in turn, the jaw members 110 and 120 for subsequent grasping or re-grasping of tissue. In one embodiment, the handles 30a and 30b may be biased in an open configuration to facilitate handling and manipulation of the jaws within an operative field. Various spring-like mechanisms are contemplated which may be utilized to accomplish this purpose.

Movable handles 30a and 30b are designed to provide a distinct lever-like mechanical advantage over conventional handle assemblies. The enhanced mechanical advantage for actuating the jaw members 110 and 120 is gained by virtue of the unique position and combination of several inter-cooperating elements which reduce the overall user forces necessary to obtain and maintain the jaw members 110 and 120 under ideal operating pressures of about 3 kg/cm$^2$ to about 16 kg/cm$^2$. Details relating to the working components the handle assembly and drive assembly are disclosed in above-mentioned U.S. patent application Ser. No. 11/540,335. In other words, it is envisioned that the combination of these elements and their positions relative to one another enables the user to gain lever-like mechanical advantage to actuate the jaw members 110 and 120 enabling the user to close the jaw members 110 and 120 with lesser force while still generating the required forces necessary to effect a proper and effective tissue seal.

As shown best in FIGS. 4A, 4B, 5 and 6, the end effector assembly 100 is designed as a bilateral assembly, i.e., both jaw members 110 and 120 pivot relative to one another about a pivot pin 185 disposed therethrough. A unilateral end effector assembly is also envisioned. End effector assembly 100 further includes a knife guide 133 that houses the knife blade 190 for translation therethrough. Knife guide 133 is assembled with flanges 113 and 123 to allow pivotable movement of the flanges 113 and 123 about a pivot pin 185 disposed between the jaw members 110 and 120 upon translation of a drive pin 180 as explained in more detail below.

More particularly, jaw members 110 and 120 include proximal flanges 113 and 123, respectively, which each include an elongated angled slot 181a and 181 b, respectively, defined therethrough. Drive pin 180 mounts jaw members 110 and 120 and knife guide 133 to the end of a rotating shaft 18 and within a cavity 17' defined at the distal ends 17a and 17b of drive actuator or sleeve 17 (See FIG. 5). Knife guide 133 includes an elongated slot 181c defined therethrough, configured for accepting the drive pin 180 and for allowing translation of the drive pin 180 within slots 181a-181c, which pivots the jaw members 110 and 120 relative to one another for grasping tissue. Knife guide 133 may also provide a unique safety feature for the forceps 10 as described in more detail below.

Upon actuation of the drive assembly 60, the drive sleeve 17 reciprocates which, in turn, causes the drive pin 180 to ride within slots 181a and 181b to open and close the jaw members 110 and 120 as desired and similarly causes the drive pin 180 to ride within slot 181c of knife guide 133. The jaw members 110 and 120, in turn, pivot about pivot pin 185 disposed through respective pivot holes 186a and 186b defined within flanges 113 and 123, the jaw members 110 and 120 and hole 186c disposed within knife guide 133. Upon actuation, knife guide 133 remains oriented in alignment with the shaft 12 as the jaws move about pivot pin 185 (See FIG. 6). As can be appreciated, squeezing handles 30a and 30b toward the housing 20 pulls drive sleeve 17 and drive pin 180 proximally to close the jaw members 110 and 120 about tissue grasped therebetween and pushing the sleeve 17 distally opens the jaw members 110 and 120 for grasping purposes.

Flanges 113 and 123 of jaw members 110 and 120, respectively, are positioned in an abutting relationship with one another and knife guide 133 is positioned adjacent to flanges 113 and 123. Flanges 113, 123 and knife guide 133 are assembled and engaged via pivot pin 185 disposed through apertures 186a, 186b, and 186c, respectively. Further, flanges 113, 123 are pivotable about one another via drive pin 180 disposed through slots 181a and 181b and of flanges 113, 123, respectively. A knife path 138 may be defined between flange 113 and knife guide 133, as shown in FIGS. 6 and 7. The knife path 138 longitudinally aligns with knife channels 115a and 115b defined within jaw members 110 and 120, such that knife blade 190 travels in a substantially straight path through knife path 138 and, further, through knife channels 115a and 115b.

Alternatively, the orientation of flanges 113 and 123 may be reversed, with knife path 138 being defined between flange 123 and blade guide 133. In contrast to prior known designs, the abutting relationship between flanges 113 and 123 (in either orientation) strengthens the jaw flanges 113 and 123 since a blade path or blade channel does not need to be defined therebetween but, rather, is defined on an exterior side of one of the flanges 113 and 123. Thus, the knife 190 travels between the blade guide 133 and the flanges 113 and 123 and not between flanges. By manufacturing the knife path 138 on either side of the flanges 113 and 123, jaw splay may also be more easily controlled and tighter tolerances may be employed during the manufacturing process, thereby allowing tighter tolerances on certain features of the jaw member 110 and 120 resulting in better overall performance.

For example, the knife channels 115a and 115b defined within the jaw members 110 and 120, respectively, may be more precisely aligned with less splay between the jaw members 110 and 120, thereby facilitating knife blade 190 translation. Moreover, the strength of the flanges 113 and 123 is enhanced as well as the union therebetween, e.g., flat-on-flat abutting flange surfaces have more surface contact making the union therebetween stronger. The knife guide 133 may also be configured to pre-load jaw members 110 and 120 to help ensure proper alignment of knife channel halves 115a and 115b upon closing of the jaw members 110 and 120 as explained in more detail below.

As best shown in FIG. 6, blade guide 133 may include a blade stop or hook 135 disposed at a distal end thereof. The blade stop 135 may be integrally associated with the knife guide 133 (FIG. 6), the purpose of which is explained immediately below, or pivotably engaged with the knife guide 133, the purpose of which is explained with reference to FIG. 9. The relationship between flanges 113 and 123 and blade guide 133 is established by pivot pin 185 disposed through apertures 186a, 186b, and 186c, respectively, and by drive pin 180 disposed through slots 181a, 181b and 181c, respectively. Accordingly, when jaw members 110, 120 are in a first, or open, position, knife guide 133 pivots such the blade stop 135 interferes with the knife path 138, thereby preventing distal translation of knife blade 190. In one embodiment, this may be accomplished by the knife guide 133 including an elongated slot 181c that is cammed when the drive pin 180 is biased in a distal-most position such that the knife guide 133 and blade stop 135 pivot thereby obstructing the knife path 138. Alternatively, the blade stop 135 may pivot relative to the knife guide 133 to obstruct the knife path 138 (See FIG. 9). In this instance, the elongated slot 181c may be constructed as a pass-through or non-engaging slot.

When handles 30a and 30b are squeezed toward the housing 20, drive sleeve 17 and drive pin 180 are pulled proximally to close the jaw members 110 and 120, which also pivots the knife guide 133 so that the blade stop 135 no longer obstructs or interferes with the knife path 138. Thus, in this embodiment, the knife guide 133, by virtue of the blade stop 135, prevents distal advancement of knife blade 190 when jaw members 110 and 120 are in the first, open position and permits distal advancement of knife blade 190 when jaw members 110 and 120 are in the second, closed position.

Alternatively, a hook (not shown) may be disposed on either of flanges 113 or 123. The hook would operate in substantially the same manner as the blade stop 135 disposed on the blade guide 133 in the embodiment discussed above. Accordingly, as jaw members 110, 120 are opened, the hook on flange 113 or 123 is pivoted into the path of knife blade 190, thereby preventing distal translation of knife blade 190. When handles 30a and 30b are squeezed toward the housing 20, drive sleeve 17 and drive pin 180 are pulled proximally to close the jaw members 110 and 120. The pulling of drive pin 180 also pivots flanges 113 and 123, thereby closing the jaw members 110 and 120 and as a result, the hook is pivoted out of the path of knife blade 190.

Figure 4B:
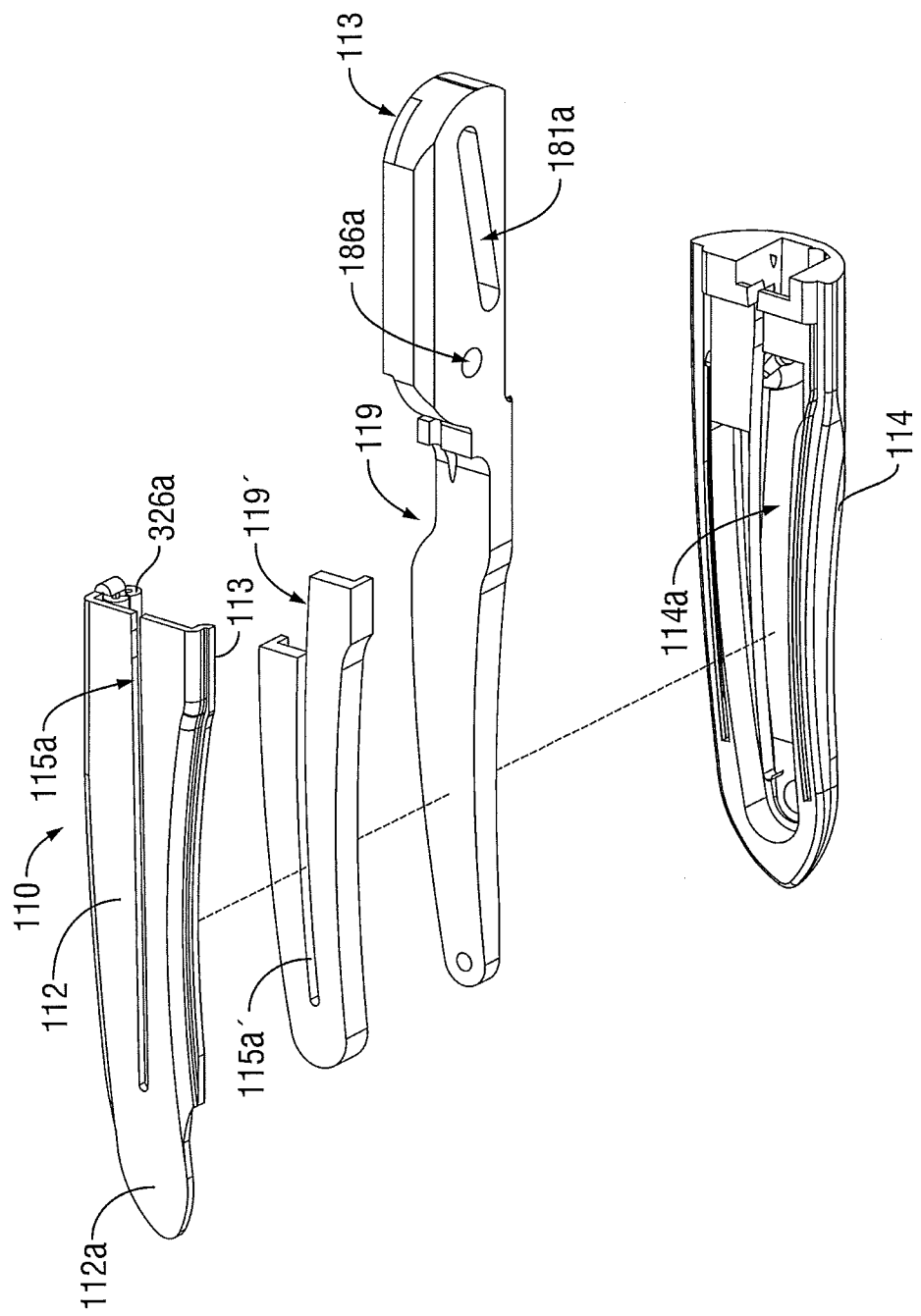
FIG. 4B is a greatly-enlarged, perspective view of the top jaw of the end effector assembly with parts separated.
Figure 5:
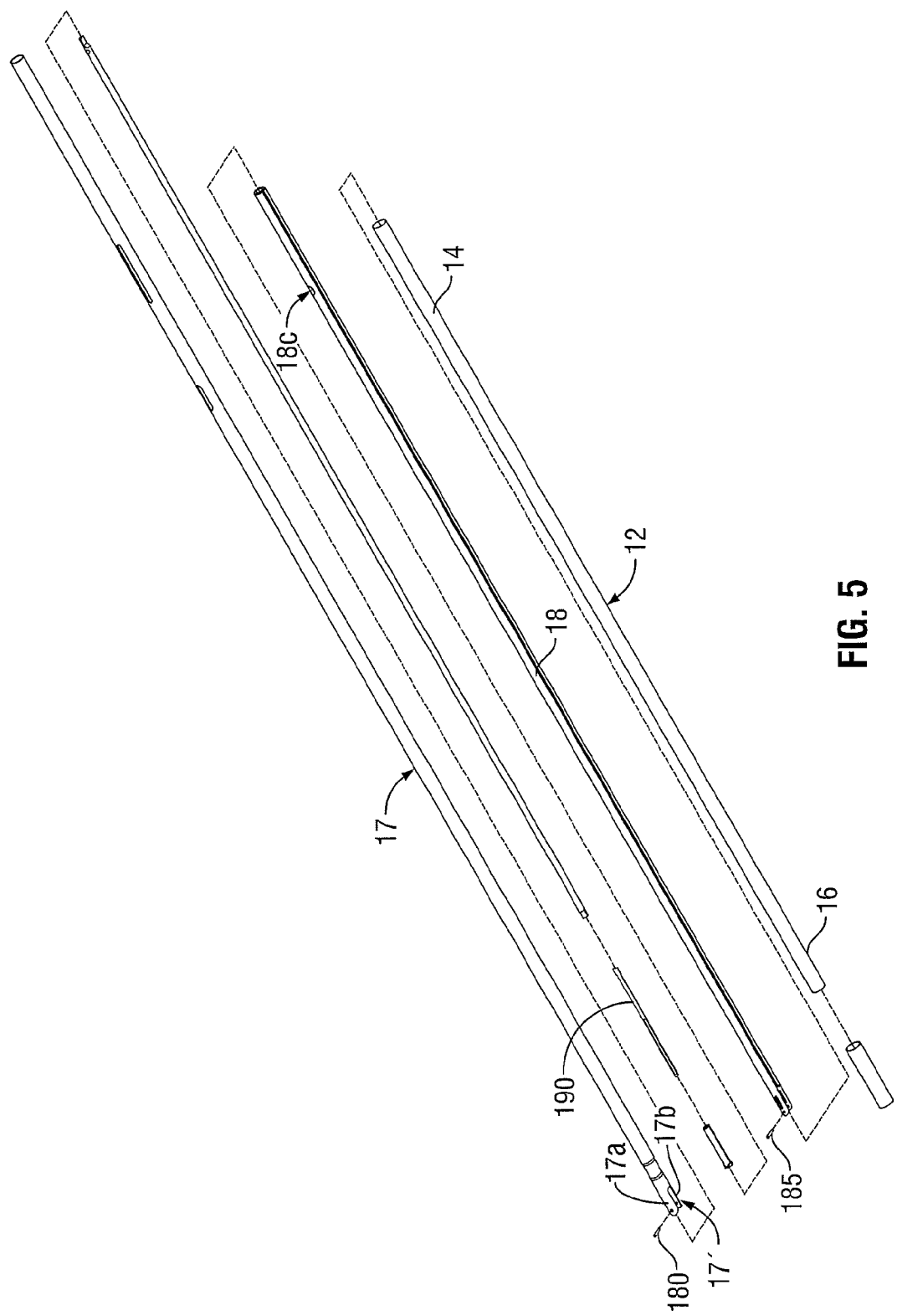
FIG. 5 is a greatly-enlarged, perspective view of the elongated shaft for housing various moving parts of the drive assembly and knife assembly.

As best shown in FIG. 4B, jaw member 110 also includes a support base 119 that extends distally from flange 113 and that is configured to support an insulative plate 119' thereon. Insulative plate 119', in turn, is configured to support an electrically conductive tissue engaging surface or sealing plate 112 thereon. Sealing plate 112 may be affixed atop the insulative plate 119' and support base 119 in any suitable manner, e.g., snap-fit, over-molding, stamping, ultrasonically welded, etc. Support base 119 together with the insulative plate 119' and electrically conductive tissue engaging surface 112 are encapsulated by an outer insulative housing 114. Outer housing 114 includes a cavity 114a that is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate. All of these manufacturing techniques produce jaw member 110 having an electrically conductive surface 112 that is substantially surrounded by an insulating substrate 114.

The electrically conductive surface or sealing plate 112 and the outer housing 114, when assembled, form longitudinally-oriented knife channel 115a defined therethrough for reciprocation of the knife blade 190. It is envisioned that the knife channel 115a cooperates with corresponding knife channel 115b defined in jaw member 120 to facilitate longitudinal extension of the knife blade 190 along a preferred cutting plane to effectively and accurately separate the tissue along the formed tissue seal. As discussed above, when knife blade 190 is deployed, at least a portion of knife blade 190 advances through knife path 138 and into knife channels 115a and 115b. In addition to the blade stop 135, handle 30a may includes a lockout flange (not shown) which prevents actuation of the knife assembly 70 when the handle 30a is open thus preventing accidental or premature activation of the knife blade 190 through the tissue. A more detailed discussion of the lockout flange is discussed in above-mentioned U.S. patent application Ser. No. 11/540,335.

As explained above and as illustrated in FIGS. 4A and 4B, in one embodiment, the knife channel 115 is formed when the jaw members 110 and 120 are closed. In other words, the knife channel 115 includes two knife channel halves—knife channel half 115a disposed in sealing plate 112 of jaw member 110 and knife channel half 115b disposed sealing plate 122 of jaw member 120. It is envisioned that the knife channel 115 may be configured as a straight slot with no degree of curvature which, in turn, causes the blade 190 to move through the tissue in a substantially straight fashion. Alternatively, and as shown, the knife channel 115 may be curved, which has certain surgical advantages. In the particular embodiment shown in FIGS. 6 and 7, the knife channel 115 (knife channel 115a shown) is curved and is offset from the centerline or longitudinal axis "A" of the forceps 10 by a distance "X" (See FIGS. 7 and 8). This offset distance "X" may be in the range of about 0.010 inches to about 0.040 inches.

The offset orientation of the knife blade 190 (by virtue or the knife guide 133 being assembled on one side of the flanges 113 and 123 allows the knife blade to enter the knife channel 115 in a substantially straight orientation thereby facilitating separation of tissue. Moreover, the knife blade 190 travels in a substantially straight manner through most of the knife channel 115 and is only forced to bend around the knife channel 115 towards a distal end of the jaw members 110 and 120. Further, the offset orientation of the knife channel, e.g., knife channel 115b, and the disposition of the knife blade 190 traveling through the knife guide 133 also enhances the cutting effect and reduces the chances of the knife blade 190 binding during translation (extension or retraction).

As mentioned above, when the jaw members 110 and 120 are closed about tissue, knife channels 115a and 115b form a complete knife channel 115 to allow longitudinal extension of the knife blade 190, from the knife path 138, in a distal fashion to sever tissue along a tissue seal. Knife channel 115 may be completely disposed in one of the two jaw members, e.g., jaw member 120, depending upon a particular purpose.

It is also envisioned that jaw member 120 may be assembled in a similar manner as described above with respect to jaw member 110.

Figure 8:
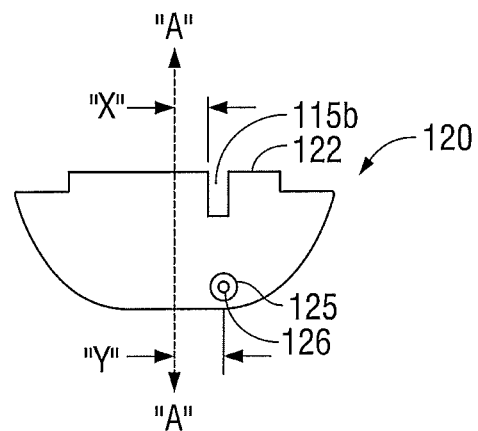
FIG. 8 is a rear, perspective view of one of the jaw members in accordance with an alternate embodiment of the present disclosure.

Referring now to FIGS. 6 and 8, electrical lead or wire 126 is shown extending from shaft 12 through knife housing 133 and entering wire tube 125 of jaw members 120. Wires 116 and 126 are used to supply electrical energy to electrically conductive sealing surfaces 112 and 122 of jaw members 110 and 120, respectively. In the embodiment of FIG. 6, knife housing 133 also acts as a wire guide, configured to guide wires 116 and 126 to jaw members 110 and 120. Electrical leads or wires 116 and 126 are protected by knife housing 133. Wire tube 125 (FIG. 8) of jaw member 120, may be offset from a longitudinal axis "Y" of the forceps 10 in the same direction as the offset knife channel 115*b*, such that knife channel 115*b* is disposed above the wire tube 125. The offset "X" of the knife channel, e.g., knife channel 115*b*, and the offset "Y" of the disposition of the electrical lead or wire 126 relative to longitudinal axis "A" may be different or the same depending upon a particular purpose or to facilitate manufacturing. For example, as mentioned above, the offset distance "X" may be in the range of about 0.010 inches to about 0.040 inches whereas the offset distance "Y" may be in the range about 0.040 inches to about 0.140 inches. In addition, particular "X" and "Y" configurations may be as follows: When "X" is about 0.010 inches "Y" may be about 0.040 inches; when "X" is about 0.017 inches "Y" may be about 0.070 inches; and when "X" is about 0.034 inches "Y" may be about 0.140 inches. Other configurations and offsets for "X" and "Y" are also contemplated and within the scope of this disclosure.

Figure 9:
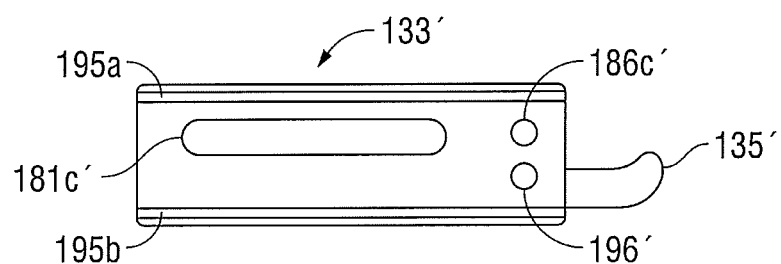
FIG. 9 is an enlarged side view of another embodiment of the knife guide according to the present disclosure.

FIG. 9 shows another embodiment of the knife guide 133' that includes similar features to the knife guide 133 described above such as elongated slot 181*c*', pivot hole 186*c*' and blade stop 135'. In this particular embodiment, the blade stop is moveable from a first position that interferes with the knife path 138 (See FIG. 7) to prevent distal translation of the knife 190 when the jaw members 110 and 120 are disposed in an first, open configuration to a second position that allows distal translation of the knife 190 when the jaw members 110 and 120 are disposed in the second, closed configuration. The blade stop 135' is pivotably engaged to the knife guide 133' and biased to obstruct with the knife path 138 when the jaw members 110 and 120 are disposed in the first, open configuration. Thus in this embodiment, the blade stop 135 prevents distal advancement of knife blade 190 when jaw members 110 and 120 are in the first, open configuration and permits distal advancement of knife blade 190 when jaw members 110 and 120 are in the second, closed configuration.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   an end effector assembly, including:
   first and second jaw members, each jaw member including a proximal flange having an inwardly-facing surface, the proximal flanges coupled to one another for moving the jaw members relative to one another between a first position and a second position for grasping tissue therebetween, the inwardly-facing surfaces of the proximal flanges disposed in abutting relation relative to one another;
   a knife configured to move along a knife path defined along an outwardly-facing surface of one of the proximal flanges, the knife movable between a refracted position and an extended position, wherein the knife extends between the jaw members to cut tissue grasped therebetween; and
   a knife guide disposed on the outwardly-facing surface of at least one of the proximal flanges, the knife guide including a blade stop pivotably coupled thereto and biased to obstruct the knife path when the first and second jaw members are disposed in a first, open configuration to prevent distal translation of knife blade.

2. The forceps according to claim 1, wherein at least one of the jaw members defines a knife channel therein, the knife channel configured to receive the knife upon movement of the knife from the retracted position to the extended position.

3. The forceps according to claim 2, wherein the knife channel is offset from a longitudinal axis defined through the end effector assembly.

4. The forceps according to claim 3, wherein the knife channel is offset from the longitudinal axis of the end effector assembly in a direction towards the knife path.

5. The forceps according to claim 1, wherein the knife guide is configured to guide movement of the knife along the knife path.

6. The forceps according to claim 1, wherein at least one of the jaw members is adapted to connect to a source of energy to communicate energy to tissue grasped between the jaw members.

7. The forceps according to claim 1, wherein the knife path extends in substantially parallel orientation relative to a longitudinal axis defined through the end effector assembly.

8. The forceps according to claim 1, wherein the knife guide is configured to guide movement of the knife along the knife path.

9. A forceps, comprising:
   an end effector assembly, including:
   first and second jaw members, at least one of the jaw members defining a knife channel extending therethrough, each jaw member including a proximal flange having an inwardly-facing surface, the proximal flanges coupled to one another for moving the jaw members relative to one another between a first position and a second position for grasping tissue therebetween, the inwardly-facing surfaces of the proximal flanges disposed in abutting relation relative to one another;
   a knife configured to move along a knife path defined along an outwardly-facing surface of one of the proximal flanges, the knife movable between a retracted position and an extended position, wherein the knife extends through the knife channel and between the jaw members to cut tissue grasped therebetween; and
   a knife guide disposed on the outwardly-facing surface of at least one of the proximal flanges, the knife guide including a blade stop pivotably coupled thereto and biased to obstruct the knife path when the first and second jaw members are disposed in a first, open configuration to prevent distal translation of knife blade.

10. The forceps according to claim 9, wherein the knife channel is offset from a longitudinal axis defined through the end effector assembly.

11. The forceps according to claim 10, wherein the knife channel is offset from the longitudinal axis of the end effector assembly in a direction towards the knife path.

12. The forceps according to claim 9, wherein at least one of the jaw members is adapted to connect to a source of energy to communicate energy to tissue grasped between the jaw members.

13. The forceps according to claim 9, wherein the knife channel and the knife path are disposed in substantial alignment with one another.

14. The forceps according to claim 9, wherein the knife path extends in substantially parallel orientation relative to a longitudinal axis defined through the end effector assembly.

* * * * *